(12) United States Patent
Hansen et al.

(10) Patent No.: US 12,138,074 B2
(45) Date of Patent: Nov. 12, 2024

(54) MONITOR DEVICE OF AN OSTOMY SYSTEM AND ASSOCIATED METHOD FOR OPERATING A MONITOR DEVICE

(71) Applicant: Coloplast A/S, Humlebaek (DK)

(72) Inventors: Jais Ask Hansen, Jaegerspris (DK); Niels Hvid, Vedbaek (DK); Finn Speiermann, Virum (DK); Lars Erup Larsen, Maaloev (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 18/100,580

(22) Filed: Jan. 24, 2023

(65) Prior Publication Data

US 2023/0233147 A1 Jul. 27, 2023

Related U.S. Application Data

(63) Continuation of application No. 16/955,044, filed as application No. PCT/DK2018/050389 on Dec. 20, 2018, now Pat. No. 11,589,811.

(30) Foreign Application Priority Data

Dec. 22, 2017 (DK) .......................... PA 2017 70989
Dec. 22, 2017 (DK) .......................... PA 2017 70990

(Continued)

(51) Int. Cl.
*A61B 5/00* (2006.01)
*A61B 90/96* (2016.01)
(Continued)

(52) U.S. Cl.
CPC .......... *A61B 5/6802* (2013.01); *A61B 5/0002* (2013.01); *A61B 5/6832* (2013.01);
(Continued)

(58) Field of Classification Search
CPC ...................................................... A61F 5/445
See application file for complete search history.

(56) References Cited

U.S. PATENT DOCUMENTS 2,327,514 A 8/1943 Fenwick
2,542,233 A 2/1951 Carroll
(Continued)

FOREIGN PATENT DOCUMENTS

CN 203786580 U 8/2014
CN 104902399 A 9/2015
(Continued)

*Primary Examiner* — Susan S Su
*Assistant Examiner* — Meagan Ngo
(74) *Attorney, Agent, or Firm* — Coloplast Corp., Coloplast A/S; Nick Baumann

(57) ABSTRACT

Disclosed is a method of operating a monitor device and an associated monitor device of an ostomy system including an ostomy appliance having an electrode assembly comprising a plurality of electrodes including a first electrode pair, the method comprising: obtaining one or more parameters including obtaining a first parameter of a first terminal pair connected to the first electrode pair of the electrode assembly; determining if one or more operability criteria are satisfied based on the one or more parameters including determining if the first parameter satisfies first operability criteria indicative of operability of the first electrode pair of the electrode assembly.

20 Claims, 13 Drawing Sheets

(30) Foreign Application Priority Data

Dec. 22, 2017 (DK) .......................... PA 2017 71002
Dec. 22, 2017 (DK) .......................... PA 2017 71006

(51) Int. Cl.
*A61B 90/98* (2016.01)
*A61F 5/44* (2006.01)
*A61F 5/443* (2006.01)
*G16H 40/63* (2018.01)

(52) U.S. Cl.
CPC .......... *A61B 5/7405* (2013.01); *A61B 5/7455* (2013.01); *A61B 90/96* (2016.02); *A61B 90/98* (2016.02); *A61F 5/4404* (2013.01); *A61F 5/443* (2013.01); *G16H 40/63* (2018.01); *A61B 2562/227* (2013.01)

(56) References Cited

U.S. PATENT DOCUMENTS

| | | | |
|---|---|---|---|
| 2,544,579 | A | 3/1951 | Ardner |
| 3,214,502 | A | 10/1965 | Schaar |
| 3,832,510 | A | 8/1974 | Pfau et al. |
| 3,915,171 | A | 10/1975 | Shermeta |
| 3,941,133 | A | 3/1976 | Chen |
| 4,231,369 | A | 11/1980 | Sorensen et al. |
| 4,372,308 | A | 2/1983 | Steer et al. |
| 4,449,970 | A | 5/1984 | Bevan et al. |
| 4,668,227 | A | 5/1987 | Kay |
| 4,754,264 | A | 6/1988 | Okada et al. |
| 4,775,374 | A | 10/1988 | Cilento et al. |
| 4,834,731 | A | 5/1989 | Nowak et al. |
| 4,973,323 | A | 11/1990 | Kaczmarek et al. |
| 4,982,742 | A | 1/1991 | Claude |
| 5,013,307 | A | 5/1991 | Broida |
| 5,016,645 | A | 5/1991 | Williams et al. |
| 5,051,259 | A | 9/1991 | Olsen et al. |
| 5,074,851 | A | 12/1991 | Plass et al. |
| 5,111,812 | A | 5/1992 | Swanson et al. |
| 5,237,995 | A | 8/1993 | Cano |
| 5,318,543 | A | 6/1994 | Ross et al. |
| 5,358,488 | A | 10/1994 | Suriyapa |
| 5,486,158 | A | 1/1996 | Samuelsen |
| 5,570,082 | A | 10/1996 | Mahgerefteh et al. |
| 5,593,397 | A | 1/1997 | La Gro |
| 5,626,135 | A | 5/1997 | Sanfilippo |
| 5,672,163 | A | 9/1997 | Ferreira et al. |
| 5,677,221 | A | 10/1997 | Tseng |
| 5,704,905 | A | 1/1998 | Jensen et al. |
| 5,790,036 | A | 8/1998 | Fisher et al. |
| 5,800,415 | A | 9/1998 | Olsen |
| 5,816,252 | A | 10/1998 | Faries et al. |
| 5,834,009 | A | 11/1998 | Sawers et al. |
| 5,879,292 | A | 3/1999 | Sternberg et al. |
| 5,942,186 | A | 8/1999 | Sanada et al. |
| 6,015,399 | A | 1/2000 | Mracna et al. |
| 6,025,725 | A | 2/2000 | Gershenfeld et al. |
| 6,103,033 | A | 8/2000 | Say et al. |
| 6,135,986 | A | 10/2000 | Leisner et al. |
| 6,171,289 | B1 * | 1/2001 | Millot .................... A61F 5/443 604/336 |
| 6,206,864 | B1 | 3/2001 | Kavanagh et al. |
| 6,407,308 | B1 | 6/2002 | Roe et al. |
| 6,433,244 | B1 | 8/2002 | Roe et al. |
| 6,482,491 | B1 | 11/2002 | Samuelsen et al. |
| 6,485,476 | B1 | 11/2002 | Von et al. |
| 6,520,943 | B1 | 2/2003 | Wagner |
| 6,677,859 | B1 | 1/2004 | Bensen |
| 6,764,474 | B2 | 7/2004 | Nielsen et al. |
| 7,066,919 | B1 | 6/2006 | Sauerland et al. |
| 7,150,728 | B2 | 12/2006 | Hansen et al. |
| 7,166,091 | B1 | 1/2007 | Zeltner |
| 7,199,501 | B2 | 4/2007 | Pei et al. |
| 7,214,217 | B2 | 5/2007 | Pedersen et al. |
| 7,326,190 | B2 | 2/2008 | Botten |
| 7,341,578 | B2 | 3/2008 | Bulow et al. |
| 7,347,844 | B2 | 3/2008 | Cline et al. |
| 7,367,965 | B2 | 5/2008 | Poulsen et al. |
| 7,559,922 | B2 | 7/2009 | Botten |
| 7,625,362 | B2 | 12/2009 | Boehringer et al. |
| 7,641,612 | B1 | 1/2010 | McCall |
| 7,670,289 | B1 | 3/2010 | McCall |
| 7,943,812 | B2 | 5/2011 | Stroebeck et al. |
| 7,981,098 | B2 | 7/2011 | Boehringer et al. |
| 8,061,360 | B2 | 11/2011 | Locke et al. |
| 8,277,427 | B2 | 10/2012 | Edvardsen et al. |
| 8,319,003 | B2 | 11/2012 | Olsen et al. |
| 8,398,575 | B1 | 3/2013 | McCall |
| 8,398,603 | B2 | 3/2013 | Thirstrup et al. |
| 8,399,732 | B2 | 3/2013 | Oelund et al. |
| 8,409,158 | B2 | 4/2013 | Edvardsen et al. |
| 8,449,471 | B2 | 5/2013 | Tran |
| 8,500,718 | B2 | 8/2013 | Locke et al. |
| 8,632,492 | B2 | 1/2014 | Delegge |
| 8,680,991 | B2 | 3/2014 | Tran |
| 8,684,982 | B2 | 4/2014 | Nguyen-Demary et al. |
| 8,740,865 | B2 | 6/2014 | Krystek et al. |
| 8,795,257 | B2 | 8/2014 | Coulthard et al. |
| 8,821,464 | B2 | 9/2014 | Hanuka et al. |
| 8,975,465 | B2 | 3/2015 | Hong et al. |
| 9,046,085 | B2 | 6/2015 | Schoess et al. |
| 9,066,812 | B2 | 6/2015 | Edvardsen et al. |
| 9,216,104 | B2 | 12/2015 | Thirstrup et al. |
| 9,308,332 | B2 | 4/2016 | Heppe |
| 9,322,797 | B1 | 4/2016 | Lastinger et al. |
| 9,629,964 | B2 | 4/2017 | Wuepper |
| 9,693,908 | B2 | 7/2017 | Eriksson et al. |
| 9,770,359 | B2 | 9/2017 | Edvardsen et al. |
| 9,788,991 | B2 | 10/2017 | Bird |
| 9,867,934 | B2 | 1/2018 | Heppe |
| 9,928,341 | B2 | 3/2018 | Angelides |
| 10,016,298 | B2 | 7/2018 | Thirstrup et al. |
| D826,740 | S | 8/2018 | Stevens et al. |
| 10,500,084 | B2 | 12/2019 | Hansen et al. |
| 10,531,977 | B2 | 1/2020 | Schoess et al. |
| 10,646,370 | B2 | 5/2020 | Keleny et al. |
| 10,792,184 | B2 | 10/2020 | Hvid et al. |
| 10,799,385 | B2 | 10/2020 | Hansen et al. |
| 10,849,781 | B2 | 12/2020 | Hansen et al. |
| 10,874,541 | B2 | 12/2020 | Seres et al. |
| 10,987,243 | B2 | 4/2021 | Thirstrup et al. |
| 11,096,818 | B2 | 8/2021 | Thirstrup et al. |
| 11,135,084 | B2 | 10/2021 | Seres et al. |
| 11,406,525 | B2 | 8/2022 | Seres et al. |
| 11,471,318 | B2 | 10/2022 | Hansen et al. |
| 11,612,512 | B2 | 3/2023 | Hansen et al. |
| 2002/0019615 | A1 | 2/2002 | Roe et al. |
| 2003/0132763 | A1 | 7/2003 | Ellenz |
| 2003/0169032 | A1 | 9/2003 | Minchole et al. |
| 2004/0006320 | A1 | 1/2004 | Buglino et al. |
| 2004/0030305 | A1 | 2/2004 | Sakamoto |
| 2004/0036484 | A1 | 2/2004 | Tamai |
| 2004/0049145 | A1 | 3/2004 | Flick |
| 2004/0078219 | A1 | 4/2004 | Kaylor et al. |
| 2004/0100376 | A1 | 5/2004 | Lye et al. |
| 2004/0106908 | A1 | 6/2004 | Leise et al. |
| 2004/0133175 | A1 | 7/2004 | Hagedorn-Olsen |
| 2004/0171999 | A1 | 9/2004 | Andersen et al. |
| 2004/0193122 | A1 | 9/2004 | Cline et al. |
| 2004/0193123 | A1 | 9/2004 | Fenton |
| 2004/0216833 | A1 | 11/2004 | Fleming et al. |
| 2005/0054997 | A1 | 3/2005 | Buglino et al. |
| 2005/0065488 | A1 | 3/2005 | Elliott |
| 2005/0070863 | A1 | 3/2005 | Bulow et al. |
| 2005/0085779 | A1 | 4/2005 | Poulsen et al. |
| 2005/0101841 | A9 | 5/2005 | Kaylor et al. |
| 2005/0240163 | A1 | 10/2005 | Andersen |
| 2005/0261645 | A1 | 11/2005 | Conrad et al. |
| 2006/0015081 | A1 | 1/2006 | Suzuki et al. |
| 2006/0025727 | A1 | 2/2006 | Boehringer et al. |
| 2006/0052752 | A1 | 3/2006 | McMichael |
| 2006/0194324 | A1 | 8/2006 | Faries et al. |
| 2006/0271002 | A1 | 11/2006 | Botten |
| 2007/0035405 | A1 | 2/2007 | Wada et al. |

(56) References Cited

U.S. PATENT DOCUMENTS

| | | |
|---|---|---|
| 2007/0135782 A1 | 6/2007 | Bager et al. |
| 2007/0185464 A1 | 8/2007 | Fattman et al. |
| 2008/0038536 A1 | 2/2008 | Strobech et al. |
| 2008/0071214 A1 | 3/2008 | Locke et al. |
| 2008/0075934 A1 | 3/2008 | Barlow et al. |
| 2008/0091154 A1 | 4/2008 | Botten |
| 2008/0140057 A1 | 6/2008 | Wood et al. |
| 2008/0234641 A1 | 9/2008 | Locke et al. |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0306459 A1 | 12/2008 | Albrectsen |
| 2009/0012501 A1 | 1/2009 | Boehringer et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0227969 A1 | 9/2009 | Jaeb et al. |
| 2009/0247970 A1 | 10/2009 | Keleny et al. |
| 2010/0010460 A1 | 1/2010 | Butler |
| 2010/0030167 A1* | 2/2010 | Thirstrup ............... A61F 5/4404 340/657 |
| 2010/0072271 A1 | 3/2010 | Thorstensson |
| 2011/0034890 A1 | 2/2011 | Stroebech et al. |
| 2011/0077497 A1 | 3/2011 | Oster et al. |
| 2011/0130642 A1 | 6/2011 | Jaeb et al. |
| 2012/0013130 A1 | 1/2012 | Jung |
| 2012/0143154 A1 | 6/2012 | Edvardsen et al. |
| 2012/0143155 A1 | 6/2012 | Edvardsen et al. |
| 2012/0258302 A1 | 10/2012 | Hunt et al. |
| 2012/0283678 A1 | 11/2012 | Nguyen-Demary et al. |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0254141 A1 | 9/2013 | Barda et al. |
| 2013/0303867 A1 | 11/2013 | Elfstrom et al. |
| 2013/0307570 A1 | 11/2013 | Bosaeus et al. |
| 2013/0324952 A1 | 12/2013 | Krystek et al. |
| 2013/0324955 A1 | 12/2013 | Wong et al. |
| 2014/0051946 A1 | 2/2014 | Arne et al. |
| 2014/0200538 A1 | 7/2014 | Euliano et al. |
| 2014/0236111 A1 | 8/2014 | Casado et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0342777 A1 | 12/2015 | Seres et al. |
| 2015/0374896 A1 | 12/2015 | Du et al. |
| 2016/0084869 A1 | 3/2016 | Yuen et al. |
| 2016/0158056 A1 | 6/2016 | Davis et al. |
| 2016/0158969 A1 | 6/2016 | McLane et al. |
| 2016/0166438 A1 | 6/2016 | Rovaniemi |
| 2016/0218555 A1 | 7/2016 | Slaby et al. |
| 2016/0235581 A1 | 8/2016 | Keleny et al. |
| 2016/0278990 A1 | 9/2016 | Chen |
| 2016/0305776 A1 | 10/2016 | Mrtensson et al. |
| 2016/0310140 A1 | 10/2016 | Belson et al. |
| 2016/0310329 A1 | 10/2016 | Patel et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0140103 A1 | 5/2017 | Angelides |
| 2017/0156920 A1 | 6/2017 | Hunt et al. |
| 2017/0340474 A1 | 11/2017 | Thirstrup et al. |
| 2017/0348137 A1 | 12/2017 | Hvid et al. |
| 2017/0348162 A1 | 12/2017 | Arizti et al. |
| 2017/0360592 A1 | 12/2017 | Carrubba |
| 2018/0049667 A1 | 2/2018 | Heppe |
| 2018/0055359 A1 | 3/2018 | Shamim et al. |
| 2018/0171183 A1 | 6/2018 | Sakurai et al. |
| 2019/0133810 A1* | 5/2019 | Seres ..................... A61F 5/443 |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0374163 A1 | 12/2019 | Faarbaek et al. |
| 2020/0100931 A1 | 4/2020 | Schoess et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Alberto |
| 2020/0306074 A1 | 10/2020 | Speiermann et al. |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0100533 A1 | 4/2021 | Seres et al. |
| 2021/0128364 A1 | 5/2021 | Cole et al. |
| 2021/0177642 A1 | 6/2021 | Andersen et al. |
| 2021/0212855 A1 | 7/2021 | Hansen et al. |
| 2021/0228194 A1 | 7/2021 | Mayberg |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |

(56) References Cited

U.S. PATENT DOCUMENTS

| | | |
|---|---|---|
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0386368 A1 | 12/2021 | Carlsson et al. |
| 2022/0000652 A1 | 1/2022 | Thirstrup et al. |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |

FOREIGN PATENT DOCUMENTS

| | | |
|---|---|---|
| CN | 104980878 A | 10/2015 |
| CN | 105588856 A | 5/2016 |
| CN | 206271160 U | 6/2017 |
| CN | 206450708 U | 8/2017 |
| DE | 3437950 A1 | 4/1985 |
| DE | 3836590 A1 | 5/1990 |
| DE | 19900611 C1 | 7/2000 |
| DE | 102011014321 A1 | 9/2012 |
| DE | 102011076219 A1 | 11/2012 |
| EP | 0168967 A1 | 1/1986 |
| EP | 0373782 A1 | 6/1990 |
| EP | 0416397 A1 | 3/1991 |
| EP | 1188157 B1 | 12/2005 |
| EP | 2108345 A1 | 10/2009 |
| EP | 2489561 A2 | 8/2012 |
| EP | 2654646 A2 | 10/2013 |
| EP | 3064179 A1 | 9/2016 |
| EP | 3213727 A1 | 9/2017 |
| GB | 2219679 A | 12/1989 |
| GB | 2225951 A | 6/1990 |
| GB | 2465742 A | 6/2010 |
| GB | 2542093 A | 3/2017 |
| JP | 04-074882 A | 3/1992 |
| JP | 06-152077 A | 5/1994 |
| JP | 09-010184 A | 1/1997 |
| JP | 2000-093448 A | 4/2000 |
| JP | 2001-087299 A | 4/2001 |
| JP | 2002-055074 A | 2/2002 |
| JP | 2002-224093 A | 8/2002 |
| JP | 2005-323981 A | 11/2005 |
| JP | 2007-319561 A | 12/2007 |
| JP | 2014-033745 A | 2/2014 |
| JP | 2014-054368 A | 3/2014 |
| JP | 2014-507182 A | 3/2014 |
| KR | 10-2012-0003987 A | 1/2012 |
| NL | 1003904 C2 | 3/1998 |
| RU | 2527155 C2 | 8/2014 |
| TW | 201201783 A | 1/2012 |
| WO | 94/15562 A1 | 7/1994 |
| WO | 97/10012 A1 | 3/1997 |
| WO | 99/33037 A1 | 7/1999 |
| WO | 99/36017 A1 | 7/1999 |
| WO | 00/79497 A1 | 12/2000 |
| WO | 01/13830 A1 | 3/2001 |
| WO | 01/50996 A1 | 7/2001 |
| WO | 02/52302 A2 | 7/2002 |
| WO | 02/99765 A1 | 12/2002 |
| WO | 2005/038693 A1 | 4/2005 |
| WO | 2005/082271 A2 | 9/2005 |
| WO | 2006/008866 A1 | 1/2006 |
| WO | 2006/094513 A2 | 9/2006 |
| WO | 2007/000168 A1 | 1/2007 |
| WO | 2007/059774 A2 | 5/2007 |
| WO | 2007/070266 A1 | 6/2007 |
| WO | 2007/098762 A1 | 9/2007 |
| WO | 2007/133555 A2 | 11/2007 |
| WO | 2008/057884 A2 | 5/2008 |
| WO | 2009/006900 A1 | 1/2009 |
| WO | 2009/052496 A1 | 4/2009 |
| WO | 2009/107011 A1 | 9/2009 |
| WO | 2009/112912 A2 | 9/2009 |
| WO | 2011/003421 A1 | 1/2011 |
| WO | 2011/004165 A1 | 1/2011 |
| WO | 2011/061540 A1 | 5/2011 |
| WO | 2011/105701 A2 | 9/2011 |
| WO | 2011/123018 A1 | 10/2011 |
| WO | 2011/139499 A1 | 11/2011 |
| WO | 2011/161254 A2 | 12/2011 |
| WO | 2012/068386 A1 | 5/2012 |
| WO | 2012/076022 A2 | 6/2012 |
| WO | 2012/084987 A2 | 6/2012 |
| WO | 2013/013197 A1 | 1/2013 |
| WO | 2014/004207 A1 | 1/2014 |
| WO | 2014/086369 A1 | 6/2014 |
| WO | 2015/007284 A1 | 1/2015 |
| WO | 2015/014774 A1 | 2/2015 |
| WO | 2015/084462 A1 | 6/2015 |
| WO | 2015/094064 A1 | 6/2015 |
| WO | 2015/187366 A1 | 12/2015 |
| WO | 2016/132738 A1 | 8/2016 |
| WO | 2016/166731 A1 | 10/2016 |
| WO | 2016/192738 A1 | 12/2016 |
| WO | 2017/023794 A1 | 2/2017 |
| WO | 2017/062042 A1 | 4/2017 |
| WO | 2017/067558 A1 | 4/2017 |
| WO | 2017/067560 A1 | 4/2017 |
| WO | 2017/074505 A1 | 5/2017 |
| WO | 2017/088153 A1 | 6/2017 |
| WO | 2017/136696 A1 | 8/2017 |
| WO | 2017/190752 A1 | 11/2017 |
| WO | 2018/028756 A1 | 2/2018 |
| WO | 2019/094635 A1 | 5/2019 |
| WO | 2019/120432 A1 | 6/2019 |
| WO | 2019/161859 A1 | 8/2019 |
| WO | 2019/161860 A1 | 8/2019 |
| WO | 2019/161863 A1 | 8/2019 |
| WO | 2019/174693 A1 | 9/2019 |
| WO | 2019/174695 A1 | 9/2019 |
| WO | 2019/213623 A1 | 11/2019 |
| WO | 2020/035121 A1 | 2/2020 |

* cited by examiner

MONITOR DEVICE OF AN OSTOMY SYSTEM AND ASSOCIATED METHOD FOR OPERATING A MONITOR DEVICE

The present disclosure relates to an ostomy system, devices thereof and method for monitoring an ostomy appliance. In particular, the present disclosure relates to a sensor assembly and/or a base plate of an ostomy system and a monitor device and associated method for.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
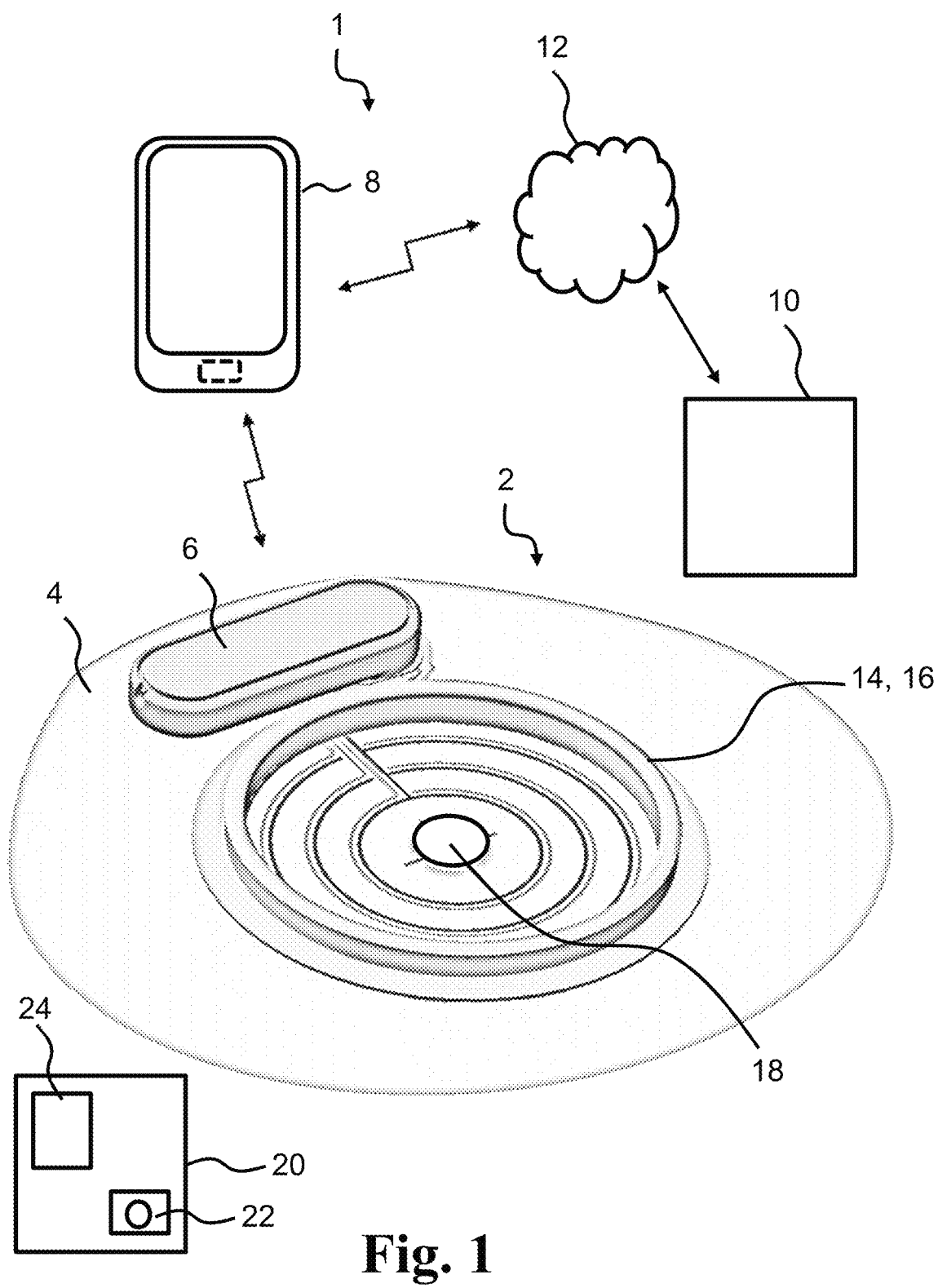
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc.

Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The ostomy appliance may comprise a sensor assembly part, such as a sensor assembly part to be applied to a base plate. For example, to allow an arbitrary base plate, such as a conventional base plate, to achieve the features as described herein. It is emphasized, that any of the features as described with respect to the base plate herein may be provided by a sensor assembly part to be applied to a base plate, e.g. by the user.

The base plate and/or the sensor assembly part may comprise a first adhesive layer, also denoted center adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate and/or the sensor assembly part to the skin surface of a user. The first adhesive layer may have a stomal opening with a center point.

The first adhesive layer may be made of a first composition. The first composition may comprise one or more polyisobutenes and/or styrene-isoprene-styrene. The first composition may comprise one or more hydrocoloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadienestyrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PI B). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethylcellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate and/or the sensor assembly part may comprise a second layer. The second layer may be an adhesive layer, also denoted rim adhesive layer. The second layer may have a second radial extension that is larger than a first radial extension of the first adhesive layer at least in a first angular range of the base plate and/or the sensor assembly part. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening with a center point.

The second adhesive layer may be made of a second composition. The second composition may comprise one or more polyisobutenes and/or styrene-isoprene-styrene. The second composition may comprise one or more hydrocoloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrenebutadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocoloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate and/or the sensor assembly part may comprise one or more electrodes, such as a plurality of electrodes, such as two, three, four, five, six, seven or more electrodes. The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals. An electrode may comprise one or more conductor parts and/or one or more sensing parts. A conductor part may be considered part of an electrode connecting two or more sensing parts, and/or connecting a sensing part with a connection part of the respective electrode. A sensing part may be considered a part of the electrode being suitable for sensing, e.g. liquid, such as liquid content, and/or output, such as output resulting from a leakage, or an imminent leakage. The sensing part may be suitable for sensing e.g. by its shape, said shape potentially being circular, oval, or rectangular. Thus, the conductor part may conduct a signal arising from the sensing part. An electrode may comprise alternating conductor parts and sensing parts. The electrode assembly may be arranged between the first adhesive layer and the second adhesive layer. The base plate and/or the sensor assembly part, e.g. the electrode assembly, may comprise a first electrode, a second electrode and optionally a third electrode. The base plate and/or the sensor assembly part, e.g. the electrode assembly, may comprise a fourth electrode and/or a fifth electrode. The base plate and/or the sensor assembly part, e.g. the electrode assembly, optionally comprises a sixth electrode. The base plate and/or the sensor assembly part, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode. The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair. The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly may have a stomal opening with a center point.

The support layer may comprise polymeric (e.g. polyurethane, PTFE, PVDF) and/or ceramic (e.g. alumina, silica) materials. In one or more exemplary base plates and/or sensor assembly parts, the support layer is made of thermoplastic polyurethane (TPU). The support layer material may be made of or comprise one or more of polyester, a thermoplastic elastomer (TPE), polyimide, polyimide, Ethylene-vinyl acetate (EVA), polyurea, and silicones.

Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part, such as the electrode assembly may comprise a masking element configured to insulate at least parts of the electrodes from the first adhesive layer of the base plate and/or the sensor assembly part. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s) A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. The masking element may comprise polymeric (e.g. polyurethane, PTFE, PVDF) and/or ceramic (e.g. alumina, silica) materials. In one or more exemplary base plates and/or sensor assembly pars, the masking element is made of or comprises thermoplastic polyurethane (TPU). In one or more exemplary base plates and/or sensor assembly parts, the masking element is made of or comprises polyester. The masking element material may be made of or comprise one or more of polyester, a thermoplastic elastomer (TPE), polyimide, polyimide, Ethylene-vinyl acetate (EVA), polyurea, and silicones.

Exemplary thermoplastic elastomers of the masking element are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part may comprise a first intermediate element. The first intermediate element may be arranged between the electrodes/electrode layer and the first adhesive layer and/or between the second layer and the first adhesive layer. The first intermediate layer may be made of an insulating material.

The base plate and/or the sensor assembly part may comprise a release liner. The release liner is a protective layer that protects adhesive layer(s) during transport and storage and is peeled off by the user prior to applying the base plate and/or the sensor assembly part on the skin. The release liner may have a stomal opening with a center point.

The base plate and/or the sensor assembly part may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening with a center point. The top layer may have a thickness in the range from 0.01 mm to 1.0 mm, e.g. in the range from 0.02 mm to 0.2 mm, such as 0.04 mm.

The base plate and/or the sensor assembly part comprises a monitor interface. The monitor interface may be configured for electrically and/or mechanically connecting the ostomy appliance (base plate and/or sensor assembly part) to the monitor device. The monitor interface may be configured for wirelessly connecting the ostomy appliance (base plate and/or sensor assembly part) to the monitor device. Thus, the monitor interface of the base plate and/or the sensor assembly part may be configured to electrically and/or mechanically couple the ostomy appliance and the monitor device.

The monitor interface of the base plate and/or the sensor assembly part may comprise, e.g. as part of a first connector of the monitor interface, a coupling part for forming a mechanical connection, such as a releasable coupling between the monitor device and the base plate and/or the sensor assembly part. The coupling part may be configured to engage with a coupling part of the monitor device for releasably coupling the monitor device to the base plate and/or the sensor assembly part.

The monitor interface of the base plate and/or the sensor assembly part may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate and/or the sensor assembly part, such as of the electrode assembly. The first intermediate element may be arranged between the terminal elements and the first adhesive layer. The first intermediate element may cover or overlap terminal element(s) of the base plate and/or the sensor assembly part when seen in the axial direction. Thus, the first adhesive layer may be protected or experience more evenly distributed mechanical stress from the terminal elements of the base plate and/or the sensor assembly part, in turn reducing the risk of terminal elements penetrating or otherwise damaging the first adhesive layer. The first intermediate element may protect or mechanically and/or electrically shield the first adhesive layer from the terminal elements of the base plate and/or the sensor assembly part.

The base plate may comprise a coupling ring or other coupling member for coupling an ostomy pouch to the base plate (two-part ostomy appliance). The center point may be defined as a center of the coupling ring.

The base plate and/or the sensor assembly part may have a stomal opening with a center point. The size and/or shape of the stomal opening is typically adjusted by the user or nurse before application of the ostomy appliance to accommodate the user's stoma. In one or more exemplary base plates and/or sensor assembly parts, the user forms the stomal opening during preparation of the base plate and/or the sensor assembly part for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate and/or the sensor assembly part coupled to the first interface. The ostomy data may comprise one or more, such as all, of first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determine an operating state of the base plate of the ostomy appliance based on one or more, such as all, of the first parameter data, the second parameter data and the third parameter data. The operating state may be indicative of a degree of radial erosion of the base plate, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate via the second interface; and/or in accordance with a determination that the operating state is a second operating state, transmit a second monitor signal comprising monitor data indicative of the second operating state of the base plate via the second interface.

In one or more exemplary monitor devices, the first operating state of the base plate corresponds to a situation wherein the first adhesive layer of the base plate and/or the sensor assembly part has experienced a first degree of radial erosion, e.g. the first adhesive layer is eroded to a first radial distance of the first electrode pair but not to a second radial distance of the second electrode pair.

In one or more exemplary monitor devices, the second operating state of the base plate corresponds to a situation wherein the first adhesive layer of the base plate and/or the sensor assembly part has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively.

In one or more exemplary monitor devices, to determine an operating state of the base plate is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by $(P\_1\_1 < TH\_1\_1)$, $(P\_2\_1 > TH\_1\_2)$, and $(P\_3\_1 > TH\_1\_3)$, wherein $P\_1\_1$ is a first primary parameter based on the first parameter data, $TH\_1\_1$ is a first primary threshold value, $P\_2\_1$ is a second primary parameter based on the second parameter data, $TH\_1\_2$ is a first secondary threshold value, P_3_1 is a third primary parameter based on the third parameter data, and TH_1_3 is a first tertiary threshold value, and wherein the first operating state is indicative of low degree of radial erosion on the base plate and/or the sensor assembly part. The first threshold values (TH_1_1, TH_1_2 and TH_1_3) may be the same or different, e.g. depending on the electrode configuration of the base plate. The first tertiary criterion (P_3_1<TH_1_3) may be omitted in the first criteria set.

The first primary parameter P_1_1 may be indicative of the resistance between the first electrode pair (first electrode and first electrode part of the ground electrode) of the base plate and/or the sensor assembly part.

The second primary parameter may be indicative of the resistance between the second electrode pair (second electrode and second electrode part of the ground electrode) of the base plate and/or the sensor assembly part.

The third primary parameter may be indicative of resistance between the third electrode pair (third electrode and third electrode part of the ground electrode) of the base plate and/or the sensor assembly part.

In one or more exemplary monitor devices, to determine an operating state of the base plate is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by $(P\_1\_1 < TH\_2\_1),$ $(P\_2\_1 < TH\_2\_2),$ and $(P\_3\_1 > TH\_2\_3)$ wherein P_1_1 is a first primary parameter based on the first parameter data and indicative of the resistance between the first electrode pair, TH_2_1 is a second primary threshold value, P_2_1 is a second primary parameter based on the second parameter data and indicative of the resistance between the second electrode pair, TH_2_2 is a second secondary threshold value, P_3_1 is a third primary parameter based on the third parameter data and indicative of the resistance between the third electrode pair, TH_2_3 is a second tertiary threshold value, and wherein the second operating state is indicative of medium degree of radial erosion on the base plate and/or the sensor assembly part. The second threshold values (TH_2_1, TH_2_2 and TH_2_3) may be the same or different, e.g. depending on the electrode configuration of the base plate and/or the sensor assembly part. The second primary criterion (P_1_1<TH_2_1) and/or the second tertiary criterion (P_3_1>TH_2_3) may be omitted in the second criteria set.

In one or more exemplary monitor devices, to determine an operating state of the base plate is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by $(P\_1\_1 > TH\_D\_1),$ $(P\_2\_1 > TH\_D\_2),$ and $(P\_3\_1 > TH\_D\_3)$ wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate and/or the sensor assembly part. The default threshold values (TH_D_1, TH_D_2 and TH_D_3) may be the same or different, e.g. depending on the electrode configuration of the base plate and/or the sensor assembly part.

In one or more exemplary monitor devices, to determine an operating state of the base plate is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate corresponds to a situation wherein the first adhesive layer of the base plate and/or the sensor assembly part has experienced a third degree of radial erosion, e.g. the first adhesive layer is eroded to the third radial distance of the third electrode pair.

The third criteria set may be given by $(P\_1\_1 < TH\_3\_1),$ $(P\_2\_1 < TH\_3\_2),$ and $(P\_3\_1 < TH\_3\_3)$ wherein P_1_1 is a first primary parameter based on the first parameter data and indicative of the resistance between the first electrode pair, TH_3_1 is a third primary threshold value, P_2_1 is a second primary parameter based on the second parameter data and indicative of the resistance between the second electrode pair, TH_3_2 is a third secondary threshold value, P_3_1 is a third primary parameter based on the third parameter data and indicative of the resistance between the third electrode pair, TH_3_3 is a third tertiary threshold value, and wherein the third operating state is indicative of high degree of radial erosion on the base plate and/or the sensor assembly part. The third threshold values (TH_3_1, TH_3_2 and TH_3_3) may be the same or different, e.g. depending on the electrode configuration of the base plate and/or the sensor assembly part. The third primary criterion (P_1_1<TH_3_1) and/or the third secondary criterion (P_2_1<TH_3_2) may be omitted in the third criteria set.

In one or more exemplary monitor devices, the ostomy data comprises fourth ostomy data from a fourth electrode pair of the base plate and/or the sensor assembly part. To apply a processing scheme may comprise to obtain fourth parameter data based on the fourth ostomy data, and determine an operating state of the base plate of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate corresponds to a situation, wherein the fourth electrode pair detects fluid, such as output, between the distal surface of first adhesive layer and the skin of the user at a fourth radial distance, and thus there is a high risk of leakage from the ostomy appliance in the fourth operating state.

The fourth criteria set may be given by (P_4_1<TH_4_4)

wherein P_4_1 is a fourth primary parameter based on the fourth parameter data and indicative of the resistance between the fourth electrode pair and TH_4_4 is a fourth quaternary threshold value, and wherein the fourth operating state is indicative of high risk of leakage from the ostomy appliance.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate and/or the sensor assembly part. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, e.g. the monitor device may form an integrated part of a base plate and/or the sensor assembly part of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

A method of operating a monitor device of an ostomy system is disclosed, such as a monitor device as disclosed above. The ostomy system may further include an ostomy appliance having an electrode assembly comprising a plurality of electrodes, such as the ostomy appliance, e.g. base plate, as disclosed above. The plurality of electrodes may include a first electrode pair. The plurality of electrodes may further comprise a second electrode pair, a third electrode pair, etc. The monitor device may comprise a processor, a memory and a first interface. The first interface may be configured for coupling to the electrode assembly of the ostomy appliance. The first interface may comprise a plurality of terminals including a first terminal pair configured for forming electrical connections with the first electrode pair of the electrode assembly.

The method of operating the monitor device may comprise obtaining one or more parameters including obtaining a first parameter of the first terminal pair connected to the first electrode pair of the electrode assembly. The method may further comprise determining if one or more operability criteria are satisfied based on the one or more parameters including determining if the first parameter satisfies first operability criteria indicative of operability of the first electrode pair of the electrode assembly.

The processor of the monitor device may be configured to carry out the steps of the disclosed method of operating a monitor device. For example, the processor of the monitor device may be configured to obtain the one or more parameters including obtaining the first parameter of the first terminal pair connected to the first electrode pair of the electrode assembly. Furthermore, the processor may be configured to determine if the one or more operability criteria are satisfied based on the one or more parameters including determining if the first parameter satisfies first operability criteria indicative of operability of the first electrode pair of the electrode assembly.

The plurality of terminals of the first interface may include a second terminal pair configured for forming electrical connections with a second electrode pair of the electrode assembly. The first terminal pair of the first interface may comprise a ground terminal and a first terminal. The second terminal pair of the first interface may comprise the ground terminal and a second terminal. Alternatively, the second terminal pair of the first interface may comprise a third terminal and the second terminal. The ground terminal may be configured for forming electrical connections with a ground electrode of the electrode assembly. The first terminal may be configured for forming electrical connections with a first electrode of the electrode assembly. The second terminal may be configured for forming electrical connections with a second electrode of the electrode assembly. The third terminal may be configured for forming electrical connections with a third electrode of the electrode assembly. The first electrode pair of the electrode assembly may comprise the ground electrode and the first electrode. The second electrode pair of the electrode assembly may comprise the ground electrode and the second electrode. Alternatively, the second electrode pair of the electrode assembly may comprise the third electrode and the second electrode.

Obtaining the one or more parameters may include obtaining a second parameter of the second terminal pair connected to the second electrode pair of the electrode assembly. Determining if the one or more operability criteria are satisfied may include determining if the second parameter satisfies second operability criteria indicative of operability of the second electrode pair of the electrode assembly.

The first parameter of the first terminal pair may be a first capacitor value, indicative of a capacitance between the first terminal pair of the first interface. The first parameter may satisfy the first operability criteria if the first capacitor value is indicative of a capacitance between the first terminal pair of the first interface above a first capacitance threshold value. The second parameter of the second terminal pair may be a second capacitor value, indicative of a capacitance between the second terminal pair of the first interface. The second parameter may satisfy the second operability criteria if the second capacitor value is indicative of a capacitance between the second terminal pair of the first interface above a second capacitance threshold value.

Alternatively or additionally, the first parameter of the first terminal pair may be a first resonance frequency value, indicative of a resonance frequency between the first terminal pair of the first interface. The first parameter may satisfy the first operability criteria if the first resonance frequency value is indicative of a capacitance between the first terminal pair of the first interface above a first resonance frequency threshold value. The second parameter of the second terminal pair may be a second resonance frequency value, indicative of a resonance frequency between the second terminal pair of the first interface. The second parameter may satisfy the second operability criteria if the second resonance frequency value is indicative of a capacitance between the second terminal pair of the first interface above a first resonance frequency threshold value.

Thus, the disclosed method allows the monitor device to assess whether one or more electrodes of the plurality of electrodes of the electrode assembly are either inoperable or damaged, or if they are working as expected. It is noted that determination of the capacitance and/or the resonance frequency does not necessitate any specific components on the base plate and/or sensor assembly part apart from the electrode layout as disclosed above used for sensing of leakage and/or erosion of adhesive.

In some situations the user may cut away one or more electrodes of the electrode assembly when adapting the stomal opening of the base plate, as described above. Thus, it is an advantage of the present disclosure that the monitor device may be adapted to determine which of the electrodes are operable, and if enough electrodes are operable to be able to detect leakage and/or erosion of adhesive.

The operability or functionality of the monitor device and/or the base plate and/or the sensor assembly part may be reported to users. Malfunctions and/or normal operation of the monitor device and/or the base plate and/or the sensor assembly part can be reported to users and other accessory devices, thereby providing warnings of possible problems. The system may be extended to also detect malfunctions or normal operation of other parts of an ostomy system, such as an accessory device and/or an ostomy pouch.

The method may comprise providing a monitor device signal indicative of a first operating failure state of the electrode assembly if the one or more operability criteria are not being satisfied.

The method may comprise providing a monitor device signal, such as a first monitor device signal and/or a second monitor device signal, indicative of an operating failure state, such as a first operating failure state and/or a second operating failure state, of the electrode assembly if the one or more operability criteria are not being satisfied. For example, the processor may be configured to provide the monitor device signal, such as the first monitor device signal and/or the second monitor device signal, indicative of an operating failure state, such as the first operating failure state and/or the second operating failure state, of the electrode assembly if the one or more operability criteria are not being satisfied. The first monitor device signal may be provided if the first operability criteria are not being satisfied and/or the second monitor device signal may be provided if the second operability criteria are not being satisfied. The monitor device signal, such as the first monitor device signal and/or the second monitor device signal, may include providing one or more of an audible signal, a tactile signal, or a wireless signal to an accessory device.

The monitor device may be configured in accordance with the results of determination of the operability criteria. For example, the method may comprise selecting a data collection scheme based on the one or more parameters. The processing unit may be configured to select a data collection scheme based on the one or more parameters. For example, selecting the data collection scheme may include selecting a first data collection scheme if the first operability criteria are not being satisfied, and selecting a second data collection scheme if the first operability criteria are being satisfied. Additionally or alternatively, selecting the data collection scheme may include selecting a first data collection scheme if the first operability criteria are not being satisfied and the second operability criteria are being satisfied, and selecting a second data collection scheme if the first operability criteria are being satisfied and the second operability criteria are being satisfied, and selecting a third data collection scheme if the first operability criteria are not being satisfied and the second operability criteria are not being satisfied, and selecting a fourth data collection scheme if the first operability criteria are not being satisfied and the second operability criteria are being satisfied.

The first data collection scheme and/or the third data collection scheme may be indicative of collection of ostomy data from the plurality of terminals excluding collection of ostomy data from the first terminal pair. The second data collection scheme and/or the fourth data collection scheme may be indicative of collection of ostomy data from the plurality of terminals including collection of ostomy data from the first terminal pair. The first data collection scheme and/or the second data collection scheme may be indicative of collection of ostomy data from the plurality of terminals excluding collection of ostomy data from the second terminal pair. The third data collection scheme and/or the fourth data collection scheme may be indicative of collection of ostomy data from the plurality of terminals including collection of ostomy data from the second terminal pair.

The data collection scheme may be indicative of which terminals from which to collect ostomy data. Thus, the method may comprise determining which terminals on the monitor device to collect the ostomy data from, e.g. based on the one or more parameters, such as whether or not one or more of the one or more operability criteria are being met.

Selecting the data collection scheme may include retrieving the data collection scheme(s) from the memory of the monitor device. Alternatively or additionally, selecting the data collection scheme may include receiving the data collection scheme(s) from an accessory device.

The method may comprise selecting a processing scheme based on the one or more parameters. The processing unit may be configured to select a processing scheme based on the one or more parameters. For example, selecting the processing scheme may include selecting a first processing scheme if the first operability criteria are not being satisfied, and selecting a second processing scheme if the first operability criteria are being satisfied. Additionally or alternatively, selecting the processing scheme may include selecting a first processing scheme if the first operability criteria are not being satisfied and the second operability criteria are being satisfied, and selecting a second processing scheme if the first operability criteria are being satisfied and the second operability criteria are being satisfied, and selecting a third processing scheme if the first operability criteria are not being satisfied and the second operability criteria are not being satisfied, and selecting a fourth processing scheme if the first operability criteria are not being satisfied and the second operability criteria are being satisfied.

Selecting the processing scheme may include retrieving the processing scheme(s) from the memory of the monitor device. Alternatively or additionally, selecting the processing scheme may include receiving the processing scheme(s) from an accessory device.

The one or more parameters may include a power parameter, e.g. indicative of a power capacity of the monitor device. Obtaining the one or more parameters may include obtaining a power parameter indicative of a power capacity, such as a power reserve, of a power unit of the monitor device. Determining if the one or more operability criteria are satisfied may include determining if the power parameter satisfies a power criteria. For example, in order to satisfy the power criteria, it may be required that the power unit of the monitor device has a sufficient power capacity to be operational for a predetermined amount of time.

The method may comprise checking an electrical signal of the power unit of the monitor device to assess the power capacity of the power unit. For example, the power capacity of the power unit may be queried, e.g. by the processor, at one or more times, e.g. periodically while the monitor device is coupled to a base plate and/or when the monitor device is decoupled from a base plate. Thereby the operability of the monitor device may be assessed. For the foregoing exemplary queries of the power capacity of the power unit, it may be determined if the power criteria are satisfied by comparing measured values to known values stored in memory.

The method may comprise obtaining ostomy data from the base plate via the first interface during a time period that the base plate is applied to a skin surface of the user, e.g. to determine a base plate application parameter indicative of application quality based on the ostomy data. Determining if the one or more operability criteria are satisfied may, alternatively or additionally, be based on the base plate application parameter. For example, determining if the one or more operability criteria are satisfied may include determining if the base plate application parameter satisfies application parameter criteria.

Hence, the user may be warned if the base plate application parameter indicates that the application quality is decreasing, e.g. below a set threshold.

The method may comprise obtaining a connection parameter indicative of mechanical connection quality between the monitor device and the base plate and/or sensor assembly part. Obtaining the one or more parameters may include obtaining the connection parameter. The one or more parameters, such as the connection parameter, may be indicative of connection, such as coupling, between the monitor device and the base plate and/or sensor assembly part. For example, the one or more parameters, such as the connection parameter, may be indicative of the monitor device being fully connected and/or coupled to the base plate and/or sensor assembly part. Determining if the one or more operability criteria are satisfied may, alternatively or additionally, be based on the connection parameter. For example, determining if the one or more operability criteria are satisfied may include determining if the connection parameter satisfies connection parameter criteria. Thus, a poorly connected monitor device, having an increased risk of experiencing a failed connection, may be indicated by the monitor device signal(s).

The monitor device may be configured to detect coupling, such as correct and/or complete coupling, between the monitor device and a target device, such as the base plate and/or the sensor assembly part and/or a docking station. The monitor device may comprise an identifier sensor configured to detect and/or query one or more identifier element(s) of the base plate and/or sensor assembly part. The identifier sensor may be a coupling sensor, such as a coupling sensor configured to detect and/or identify an identifier element of the target device and/or configured to detect complete coupling of the monitor device to the target device.

The identifier sensor may be configured to generate a coupled signal indicative of the monitor device being coupled, such as correctly and/or completely coupled, to the target device. Alternatively or additionally, the identifier sensor may be configured to generate an identifier signal. The identifier signal may be indicative of the target device, such as which target device is coupled to the monitor device and/or whether the target device is coupled, such as correctly and/or completely coupled, to the monitor device. The processor may be configured to receive the coupled signal and/or the identifier signal from the identifier sensor. The processor may be configured to determine whether the monitor device is coupled, such as completely and/or correctly coupled, to the target device, e.g. based on the identifier signal.

In embodiments, the processor of the monitor device is configured to determine an operating failure type from a set of operating failure types stored in the memory. More particularly, in embodiments the processor may be configured to assess the nature of an operability failure, such as an inoperable electrode and/or a low power capacity. Thereafter a monitor device signal indicative of the operating failure type may be provided.

By way of example, the monitor device can provide a warning for an inoperable electrode that is distinct from a warning for a low power capacity. Accordingly, the processor checks for operability issues and compares readings to known parameter criteria stored in the memory, and as necessary, references alert conditions and warnings that are also stored in memory, and then notifies the user as may be appropriate.

The method may comprise determining an operating failure type from a set of operating failure types. Providing the first monitor device signal may include providing the first monitor device signal indicative of the operating failure type. Thereby, the user may be assisted in solving an error causing the failure and/or the user may be provided with information of the status of operability. The first monitor device signal may indicate that a component of the ostomy appliance, e.g. the base plate, the sensor assembly part, an ostomy pouch, etc., is one or more of inoperative, damaged, defective, improperly connected or improperly attached. Alternatively or additionally, the method may further comprise in accordance with the operability criteria being satisfied, providing a second monitor device signal indicative of correct operation of the base plate and/or the sensor assembly part. For example, if the operability evaluation does not result in a finding of an operability problem, a notification may be provided, such as to the user, that the monitor device and/or base plate and/or sensor assembly part are functioning correctly. The processor may check the memory for notification types for the second monitor device signal, which can be one or more of an audible signal through a loudspeaker of the monitor device, a tactile signal through a haptic feedback element, or a wireless signal to an accessory device, such as a phone or a wearable item, e.g. a watch, wrist band or ring, that then may alert the user.

The present disclosure provides several advantages, among others the operability or functionality of the monitor device and/or base plate and/or other devices may be tested for operability, and the monitor device may be configured accordingly and/or the user or accessory devices may be informed. For example, a determination of the operability of one or more electrodes can be assessed. The assembly/coupling of the monitor device to an ostomy appliance such as a base plate can be assessed. The monitor device can assess whether the base plate has been properly applied to the user's skin surface.

Mechanical connections between the monitor device and base plate can be assessed. Battery capacity or other power characteristics of the monitor device can be assessed. Malfunctions and/or normal operation of the ostomy appliance and monitor device can be reported to users and other accessory devices, thereby providing warnings of possible problems.

Furthermore, more effective operation of the monitor device may be achieved by regulating data collection and/or processing schemes more effectively. For example, detection and/or identification of operable and/or inoperable electrodes may facilitate more accurate interpretation of data collected by the ostomy system.

FIG. 1 illustrates an exemplary ostomy system. The ostomy system 1 comprises an ostomy appliance 2 including a base plate 4 and an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device.

Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate has a stoma-receiving opening 18 with a stoma center point. The size and/or shape of the stomal opening 18 is typically adjusted by the user or nurse before application of the ostomy appliance to accommodate the user's stoma.

The ostomy system 1 optionally comprises a docking station 20 forming an accessory device of the ostomy system 1. The docking station comprises 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
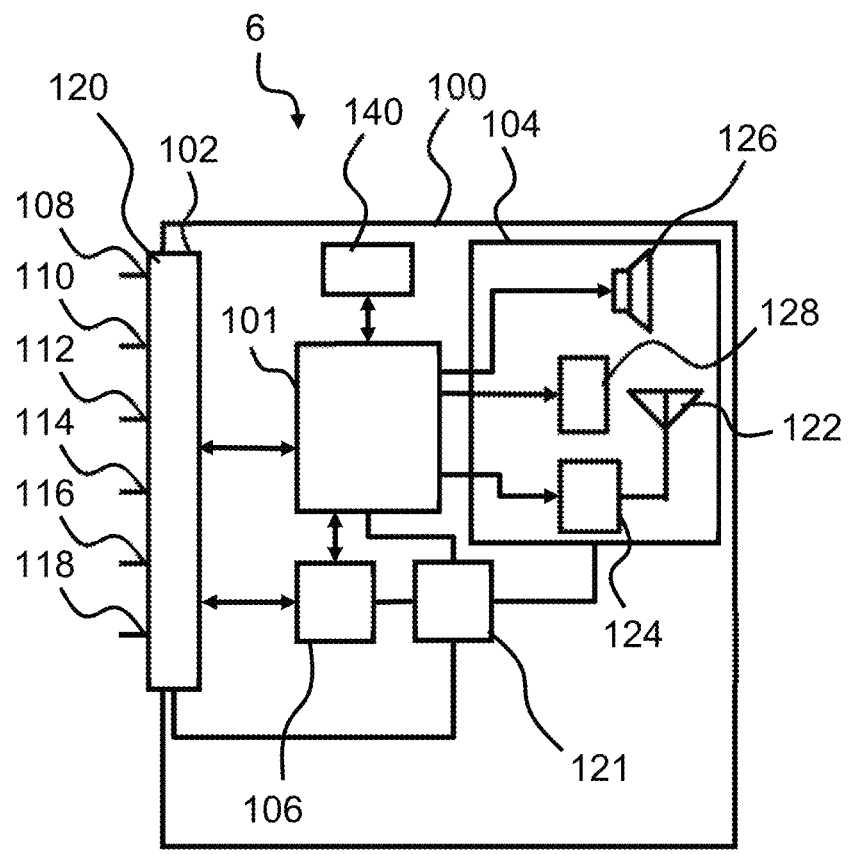
FIG. 2 illustrates an exemplary monitor device of the ostomy system.

FIG. 2 is a schematic block diagram of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 comprises a sensor unit 140 connected to the processor 101. The sensor unit 140 comprises a temperature sensor for feeding temperature data to the processor and a G-sensor or accelerometer for feeding acceleration data to the processor 101.

The processor 101 is configured to apply a processing scheme, and the first interface 102 is configured for collecting ostomy data from the base plate coupled to the first interface, the ostomy data comprising first ostomy data from a first electrode pair of the base plate, second ostomy data from a second electrode pair of the base plate, and third ostomy data from a third electrode pair of the base plate. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate of the ostomy appliance based on one or more, e.g. all, of the first parameter data, the second parameter data and the third parameter data, wherein the operating state is indicative of a degree of radial erosion of the base plate and/or acute leakage risk for the ostomy appliance. The monitor device 6 is configured to, in accordance with a determination that the operating state is a first operating state, transmit a first monitor signal comprising monitor data indicative of the first operating state of the base plate via the second interface; and in accordance with a determination that the operating state is a second operating state, transmit a second monitor signal comprising monitor data indicative of the second operating state of the base plate via the second interface.

The processor 101 may receive identification information, such as base plate identification information through the first interface 102 via terminals 108, 110, 112, 114, 116, 118. For example, the identification information may be represented by identifier elements of an electrode configuration. The processor 101 may receive the identification information in the form of one or more resistance values, one or more capacitance values, one or more multiple bit digital values or by other techniques. The identification information may be representative of one or more of base plate and/or sensor assembly part type, manufacturing batch, manufacture date, and/or a unique identifier.

In some implementations, following receipt of the identification information, the processor 101 may transmit the identification information by second interface 104, such as by the wireless transceiver 124 to the accessory device 8 and/or docking station 20, and/or the processor 101 may store the identification information in the memory 106, and/or the processor 101 may process the identification information.

The processor 101 may determine a data collection scheme based on the identification information, and/or the processor 101 may determine the data collection scheme by accessing the data collection scheme from memory 106 and/or by receiving the data collection scheme through the wireless transceiver 124. In some examples, the processor 101 may receive the data collection scheme from accessory device 8 and/or docking station 20. In the same or different implementations, the processor 101 may receive the data collection scheme from a remote server, e.g., via accessory device 8 and/or docking station 20. In implementations where the processor 101 receives the data collection scheme through the wireless transceiver 124, processor 101 may store the received data collection scheme in the memory 106 for subsequent access. The processor 101 may retrieve the data collection scheme from the memory 106 for preforming data collection according to the data collection scheme.

For example, in some implementations, the processor 101 determines the data collection scheme by determining which of terminals 108, 110, 112, 114, 116, 118 on the monitor device 6 to collect the ostomy data from. In the same or different implementations, the processor 101 determines the timing of the ostomy data collection. In various implementations, the processor 101 controls the collection of the ostomy data based on either or both of the determined terminals on the monitor device 106, and the determined timing.

In some implementations, the data collection scheme may include conductor integrity testing. For example, capacitance and/or resonance frequency may be measured between pairs of terminals 108, 110, 112, 114, 116, 118, such as to determine their respective operability.

In the same or different implementations, the processor 101 may determine a processing scheme based on the base plate and/or sensor assembly part identification information. In some implementations the processor 101 determines the processing scheme by receiving the processing scheme through the transceiver 124 of second interface 104, e.g., from an accessory device and/or docking station. In such implementations, the processor 101 may store the processing scheme in the memory 106 for later retrieval.

The processor may 101 receive ostomy data representative of a condition of the ostomy appliance from the base plate and/or a sensor assembly part. The processor 101 may store the operating state and/or monitor data based on the ostomy data in memory 106 and/or transmit the operating state via second interface 104, e.g. with transceiver 124 of second interface 104, to an accessory device and/or a docking station.

Figure 3:
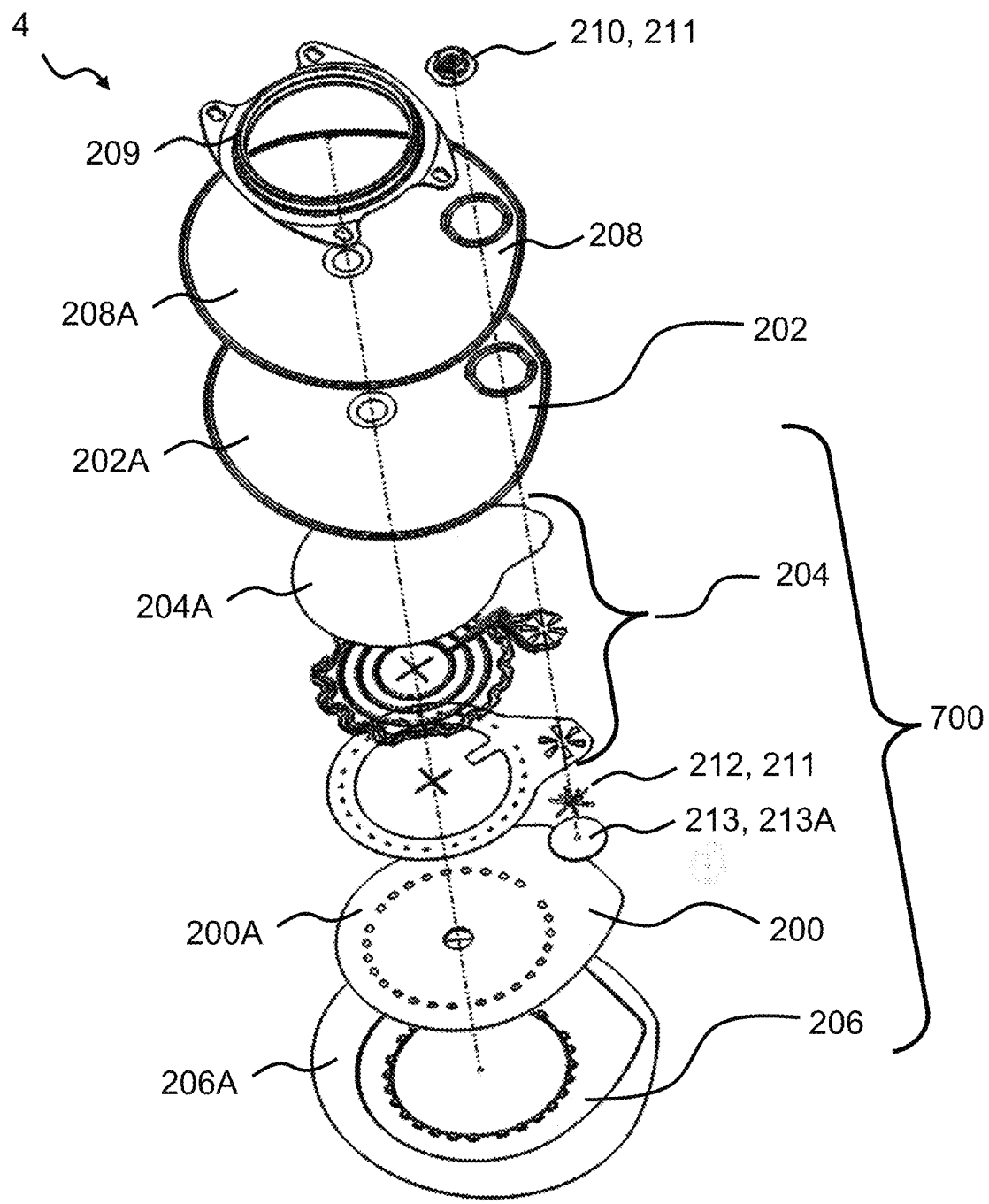
FIG. 3 is an exploded view of a base plate of an ostomy appliance.

FIG. 3 illustrates an exploded view of an exemplary base plate of an ostomy appliance. The base plate 4 comprises a first adhesive layer 200. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with electrodes formed on a proximal surface of the support layer. The base plate 4 comprises a release liner 206 that is peeled off by the user prior to applying the base plate 4 on the skin. The base plate 4 comprises a top layer 208 and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the distal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate.

Figure 4:
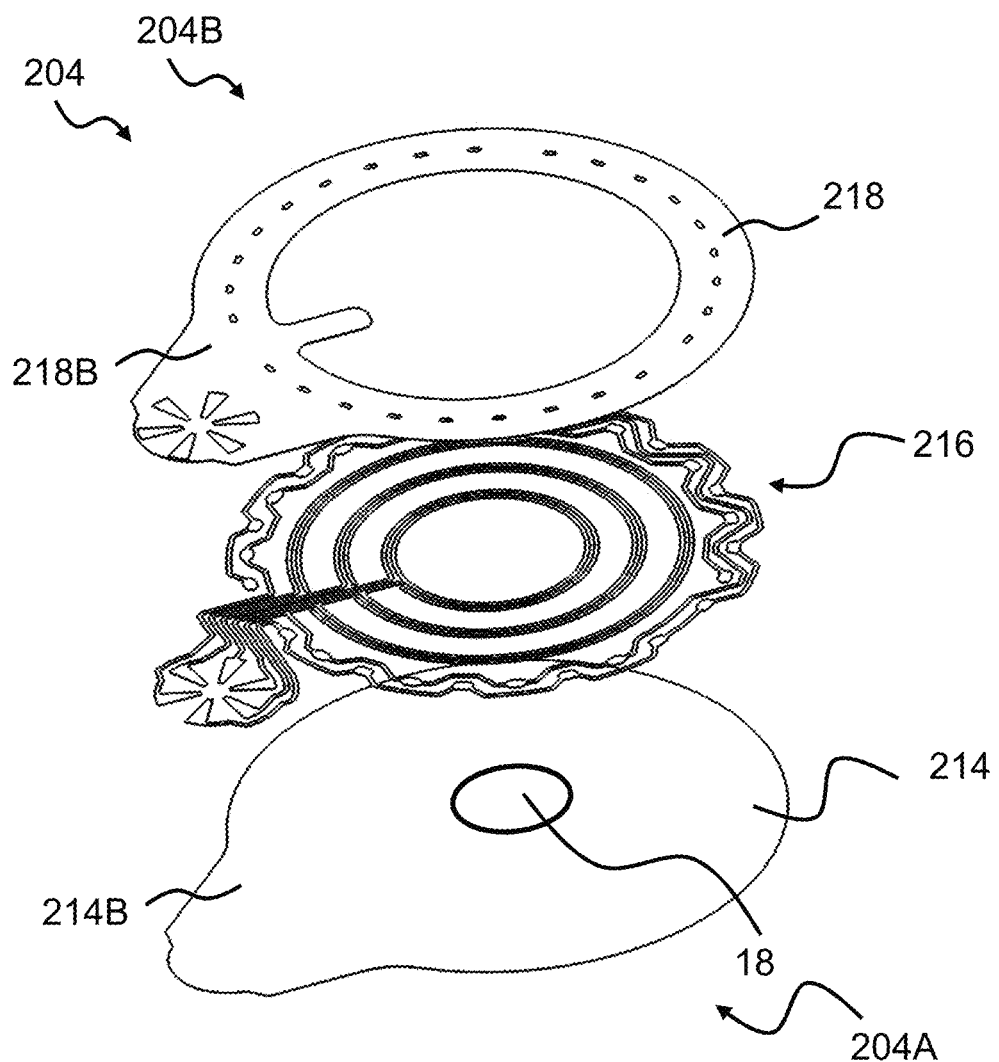
FIG. 4 is an exploded view of an exemplary electrode assembly.

FIG. 4 illustrates an exploded view of an exemplary electrode assembly 204 of a base plate and/or a sensor assembly part. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part for connecting the electrodes to respective terminal elements of the monitor interface. Further, electrode assembly 204 comprises a masking element 218 with proximal surface 218B and configured to insulate electrode parts of electrodes 216 from the first adhesive layer of the base plate and/or of the sensor assembly part. The masking element 218 covers or overlap with parts of the electrodes 216 when seen in the axial direction.

Figure 5:
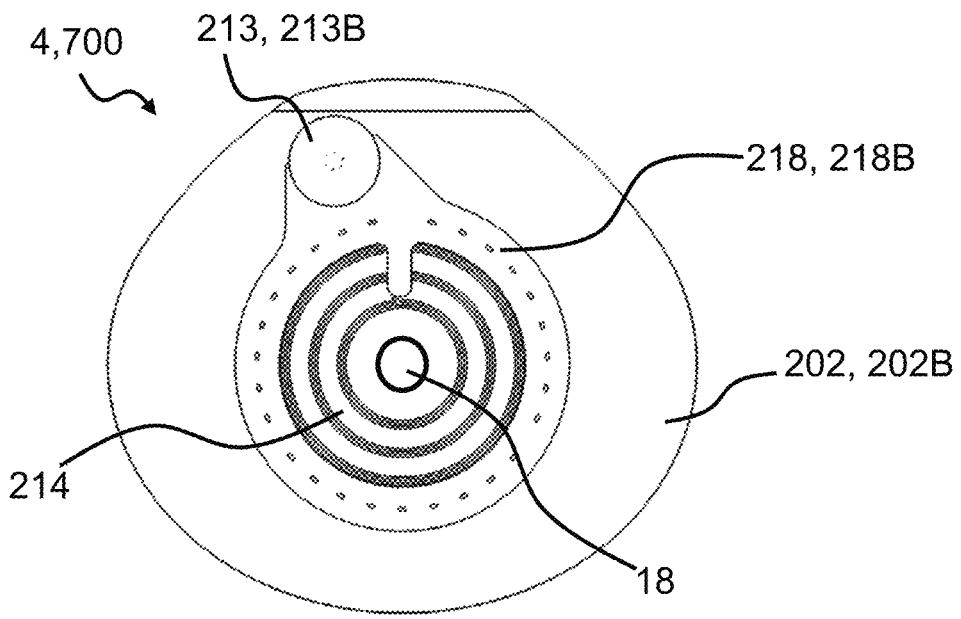
FIG. 5 is a proximal view of parts of a base plate and/or a sensor assembly part.

FIG. 5 is a proximal view of proximal surfaces of base plate parts of the base plate and/or the sensor assembly part without the first adhesive layer and the release liner. The base plate 4 and/or the sensor assembly part 700 comprises a first intermediate element 213 on the distal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate and/or the sensor assembly part.

Figure 6:
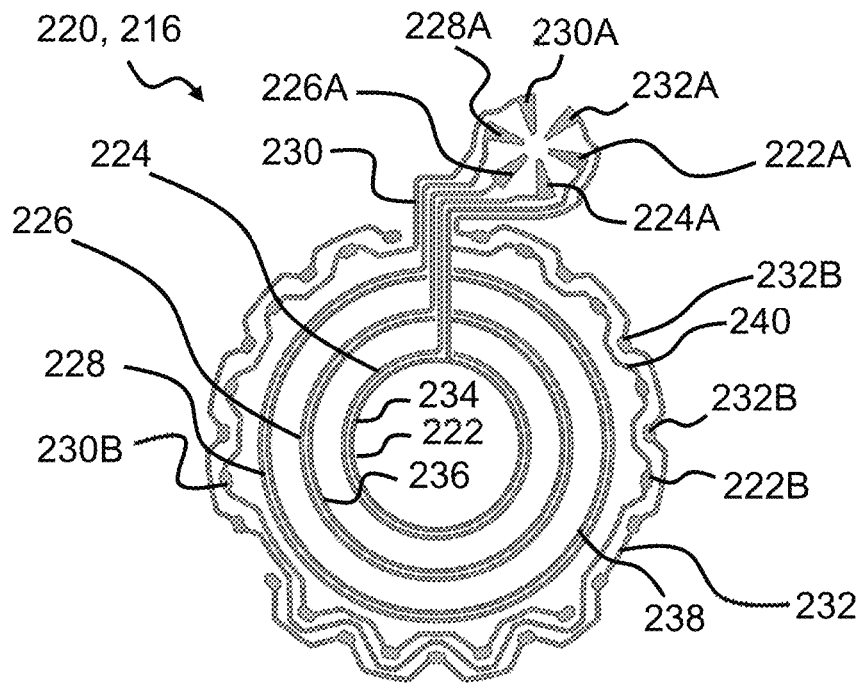
FIG. 6 is a distal view of an exemplary electrode configuration.

FIG. 6 is a distal view of an exemplary electrode configuration 220 of electrodes 216 of the electrode assembly 204. The electrode configuration 220/electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

Figure 7:
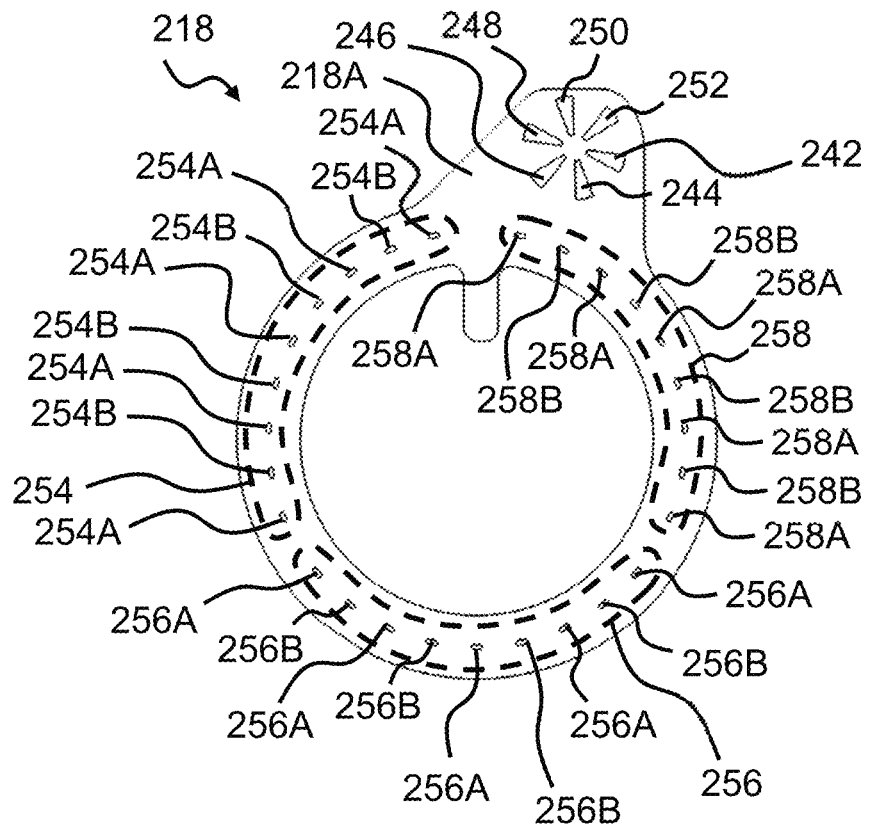
FIG. 7 is a distal view of an exemplary masking element.

The ground electrode 222 comprises a first electrode part 224 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
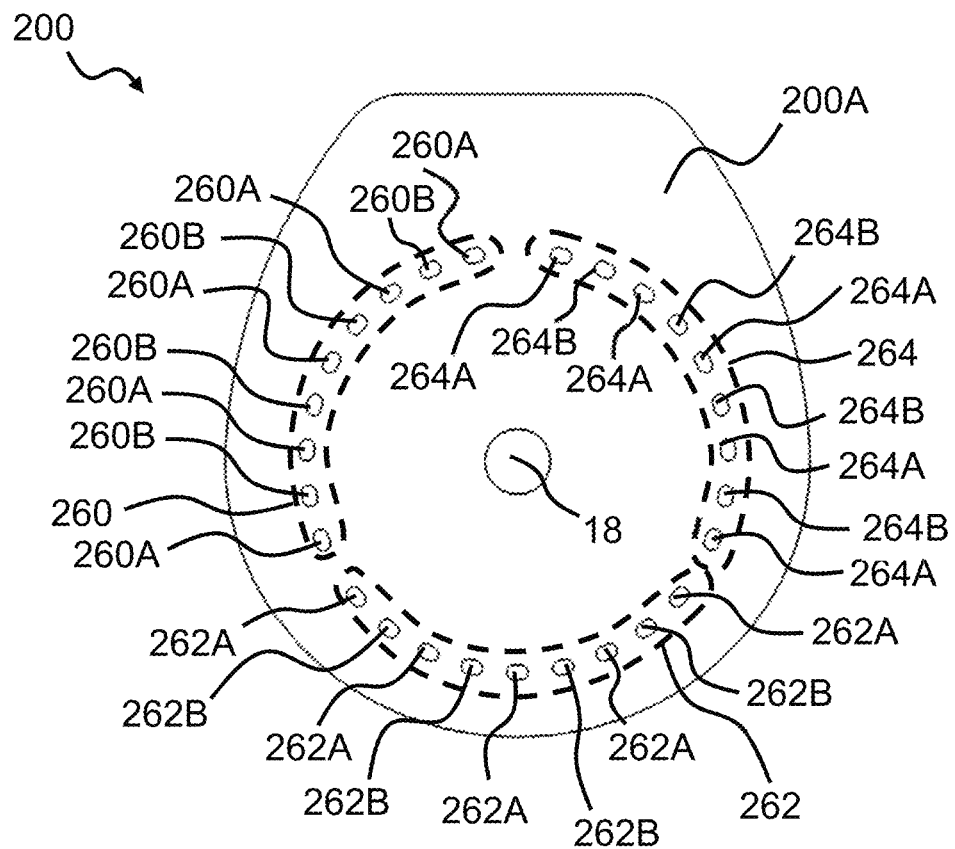
FIG. 8 is a distal view of an exemplary first adhesive layer.
Figure 9:
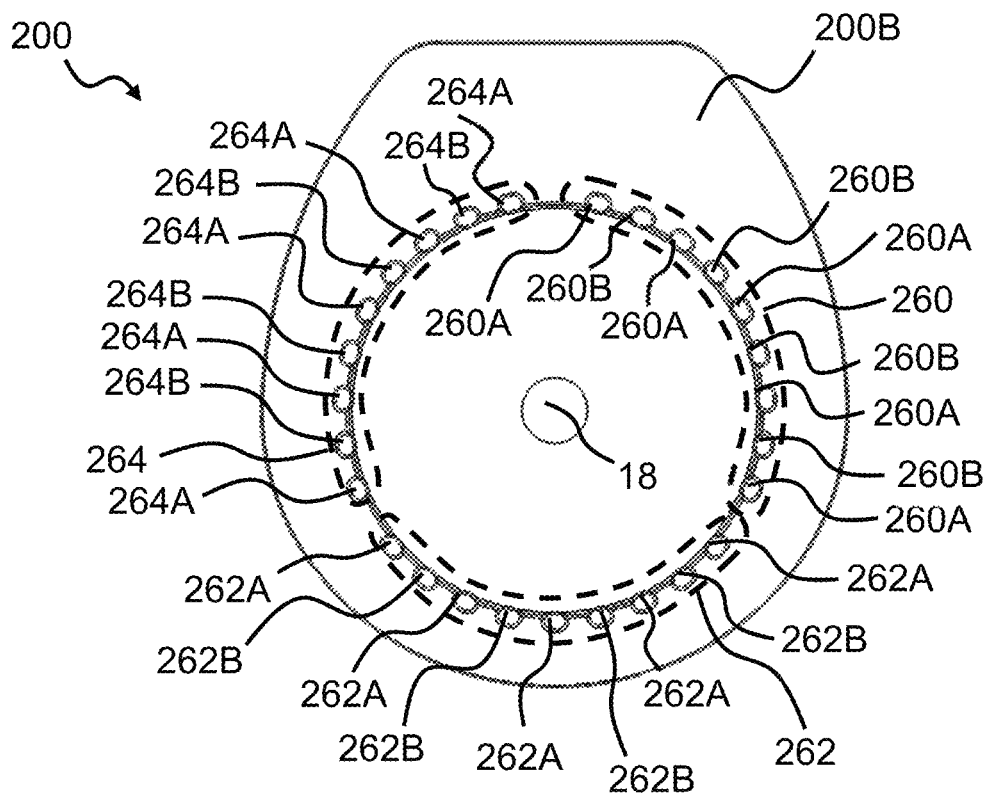
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232. The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
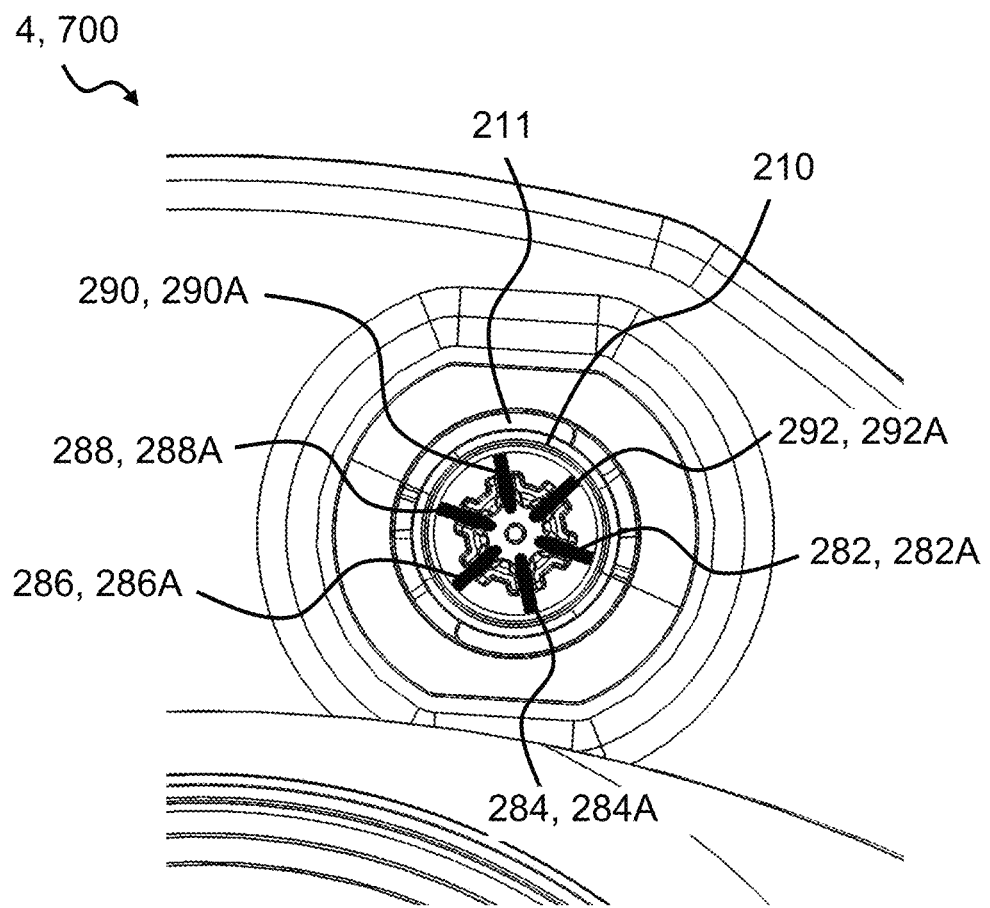
FIG. 10 is a distal view of a part of the base plate and/or the sensor assembly part including monitor interface.

FIG. 10 is a more detailed distal view of a part of the base plate 4 and/or the sensor assembly part 700. The base plate 4 and/or the sensor assembly part 700 comprises a monitor interface. The monitor interface of the base plate comprises the first connector 211. The first connector 211 comprises coupling part 210 configured to releasably couple the monitor device to the base plate and thus forming a releasable coupling. The first connector 221/monitor interface comprises a plurality of terminals formed by respective terminal elements for forming respective electrical connections with respective terminals of the monitor device.

The plurality of terminals of the first connector 211/ monitor interface comprises a ground terminal element 282 forming a ground terminal 282A, a first terminal element 284 forming a first terminal 284, a second terminal element 286 forming a second terminal 286A, and a third terminal element 288 forming a third terminal 288A. The monitor interface optionally comprises a fourth terminal element 290 forming a fourth terminal 290A and/or a fifth terminal element 292 forming a fifth terminal 292A. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate, the number of terminals and the position of the terminals in the coupling part may be adapted to the electrode configuration used in the electrode assembly of the base plate.

Figure 11:
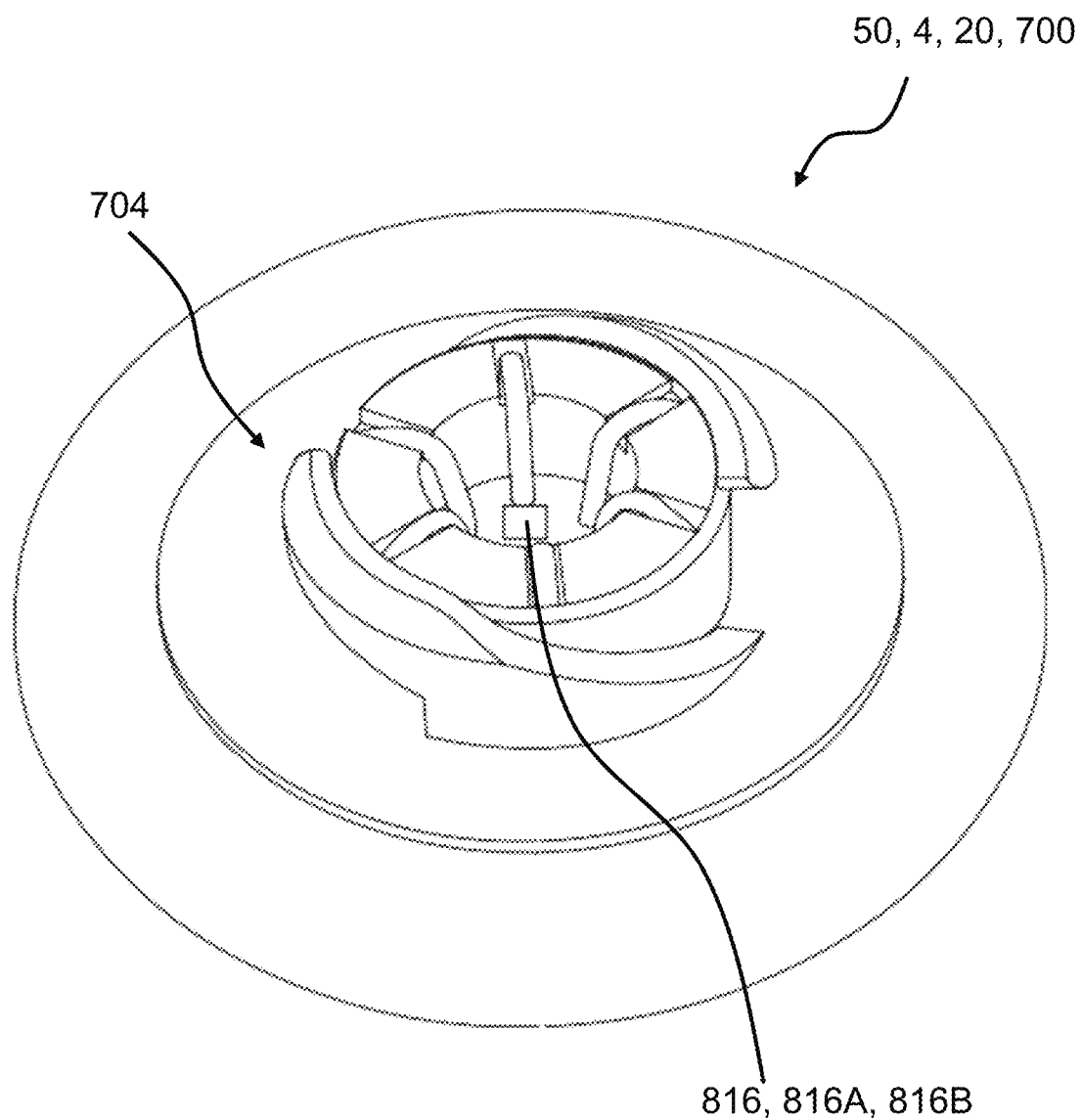
FIG. 11 illustrates an exemplary target device having an identifier element, FIG. 12 schematically illustrates an exemplary monitor device, FIG. 13 schematically illustrates an exemplary electrode configuration.

FIG. 11 illustrates an exemplary target device 50 having an identifier element 816. The target device 50 comprises a target device coupling part 704 configured to releasably and structurally couple the target device 50 to a monitor device. The target device 50 may be a base plate 4, or a sensor assembly part 700 for a base plate, as exemplified in relation to previous figures, e.g. FIG. 3. Alternatively, the target device 50 may be a docking station 20 as described in relation to previous figures, e.g. FIG. 1. The target device 50 may be one of a plurality of base plates, sensor assembly parts and/or docking stations. The target device 50 may be any device configured to be received by the monitor device. For example, one of the one or more base plates may comprise a base plate identifier element 816A, such as a base plate identifier element, whereas the docking station may comprise a docking station identifier element 816B, such as a docking station identifier element 816B. The others of the one or more base plates may each comprise another identifier element. The identifier element 816 of the target device 50 may be configured to engage with an identifier sensor of the monitor device, e.g. when the target device 50 is coupled to the monitor device. Additionally or alternatively, the identifier element 816 may be configured to be detected or identified by the identifier sensor of the monitor device such that the monitor device may identify which target device 50 (e.g. which of the plurality of base plates, sensor assembly parts or the docking stations) is being coupled to the monitor device.

As illustrated in FIG. 11, the identifier element 816 may be centrally disposed on or in the coupling part 704 of the target device 50. However, any reasonable disposition of the identifier element 816 on the target device 50 may be considered.

Figure 12:
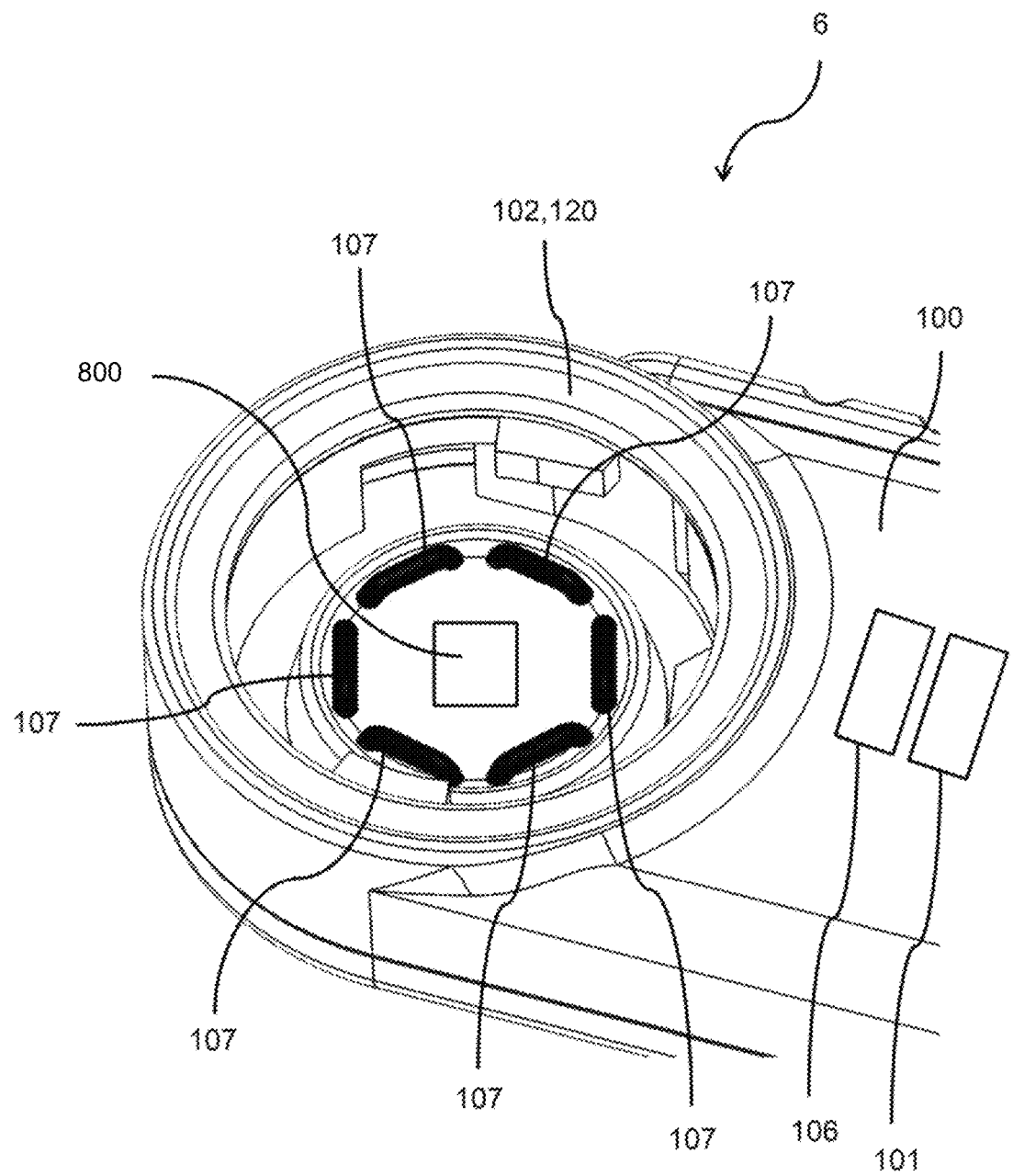

FIG. 12 schematically illustrates an exemplary monitor device 6. The monitor device 6 includes a housing 100, a processor 101, a first interface 102 and memory 106. The first interface 102 includes a coupling part 120 and a plurality of terminals 107. The coupling part 120 may be configured to releasably and structurally couple the monitor device 6 to the coupling part 210 of a base plate and/or a sensor assembly part, such as a base plate and/or sensor assembly part as described in relation to other figures. In addition, the plurality of terminals 107 of the monitor device 6 may be configured to be electrically coupled to respective terminals of the base plate and/or sensor assembly part. More particularly, the plurality of terminals 107 of the monitor device 6 may be configured to form electrical connections with the plurality of terminals 282, 284, 286, 288, 290 and 292 of the base plate 4 and/or sensor assembly part 700, e.g. as shown in FIG. 10. The coupling part 120 may also be configured to releasably and/or structurally couple the monitor device 6 to a docking station.

The monitor device 6 includes an identifier sensor 800. The identifier sensor 800 may be configured to detect and/or identify an identifier element of a target device, such as a base plate, sensor assembly part and/or docking station. The identifier sensor 800 may be a coupling sensor configured to detect coupling, such as correct and/or complete coupling, between the monitor device 6 and a target device, such as the base plate and/or the sensor assembly part and/or a docking station. Additionally or alternatively, the identifier sensor 800 may be configured to identify the target device that is being coupled to the monitor device 6. For example, the detection or identification may be performed when the monitor device 6 is coupled to the target device. Alternatively or additionally, the detection and/or identification may be performed without the monitor device 6 being coupled to the target device.

The identifier sensor 800 may be configured to cooperate with an identifier element, such as the identifier element 816 as illustrated in FIG. 11. More particularly, the monitor device identifier sensor 800 may form an electrical connection to the identifier element 816 as illustrated in FIG. 11. Accordingly, the processor 101 is configured to evaluate a connection parameter indicative of a mechanical connection quality between the monitor device 6 and the target device. In addition, an electrical connection between the monitor device 6 and the target device can also be assessed. Therefore, the processor 101 can determine if operability criteria are satisfied based on one or more connection parameters, e.g. as compared to accepted values that are stored for reference in the memory 106.

As illustrated, the identifier sensor 800 may be centrally disposed on or in the coupling part 120 of the monitor device 6. However, any reasonable disposition of the identifier sensor 800 may be considered (e.g. on or in the housing 100).

Figure 13:
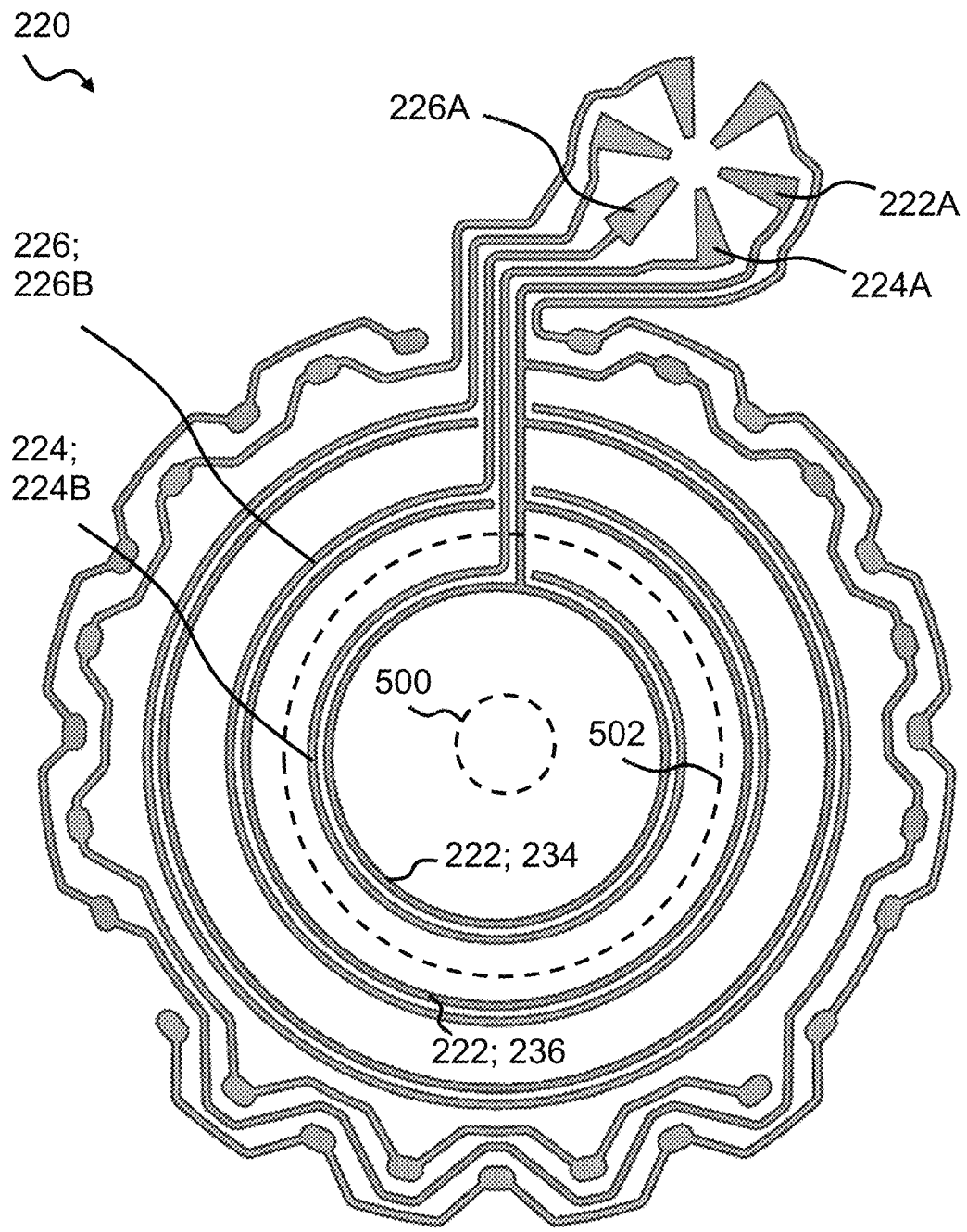

FIG. 13 schematically illustrates an exemplary electrode configuration 220 of an electrode assembly, such as the electrode configuration 220 as shown in FIG. 6, of electrode assembly 204.

The electrode configuration 220 comprises a ground electrode 222 and a first electrode 224 forming a first electrode pair. The electrode configuration 220 also comprises a second electrode 226 forming a second electrode pair together with the ground electrode 220. Also a third electrode pair formed by the ground electrode 222 and a third electrode, a fourth electrode pair formed by the ground electrode 222 and a fourth electrode, and a fifth electrode pair formed by the ground electrode 222 and a fifth electrode, as well a sixth electrode pair formed by the fifth electrode and a sixth electrode is seen. However, for simplicity these are not specifically denoted in FIG. 13.

FIG. 13 further includes indications of exemplary stomal openings, which may be cut by the user of the base plate. For example, a user may cut a stomal opening as indicated by dashed line 500, while another user may cut a stomal opening as indicated by the other dashed line 502. In the situation, where the user has cut the stomal opening along the inner dashed line 500, all electrodes remains intact, and the monitor device may reasonably collect data from all electrodes and determine an operating state of the base plate based on data collected from all electrodes, such as all electrode pairs. However, in the other situation, where the user has cut the stomal opening along the second dashed line 502, the first electrode pair comprising the ground electrode 222 and the first electrode 224, will be cut away, more specifically, the first part 234 of the ground electrode 222 and the sensing part 224B of the first electrode 224 will be removed. Thus, monitoring the first electrode 224 will not reveal anything meaningful in terms of erosion or leakage of the base plate. Therefore, it will be advantageous if the monitor device is able to detect whether and which of the electrodes are operable and may be used in determining the operating state of the base plate.

To detect whether a specific pair of electrodes are operable, the monitor device may initially query the respective pair of electrodes by measuring capacitance and/or resonance frequency between the pair of electrodes. For example, the monitor device may obtain a first parameter, such as capacitance and/or resonance frequency, of the first terminal par connected to the first electrode pair, e.g. the first electrode 224 and the ground electrode 222. If the first parameter, e.g. the capacitance and/or the resonance frequency, is not within an expected range, the monitor device may determine that the first electrode pair, e.g. the first electrode 224 and the ground electrode, is inoperable. For example, in the situation as described before where the user has cut the stomal opening as indicated by the second dashed line 502, the capacitance will be lower than the expected capacitance and/or the resonance frequency will be higher than expected, since a significant part of the first electrode 224 and the ground electrode 222 has been removed. Thereby, the monitor device may determine that the first electrode 224 and/or the first electrode pair is inoperable, and the monitor device may be configured to only monitor the remaining electrodes.

Figure 14:
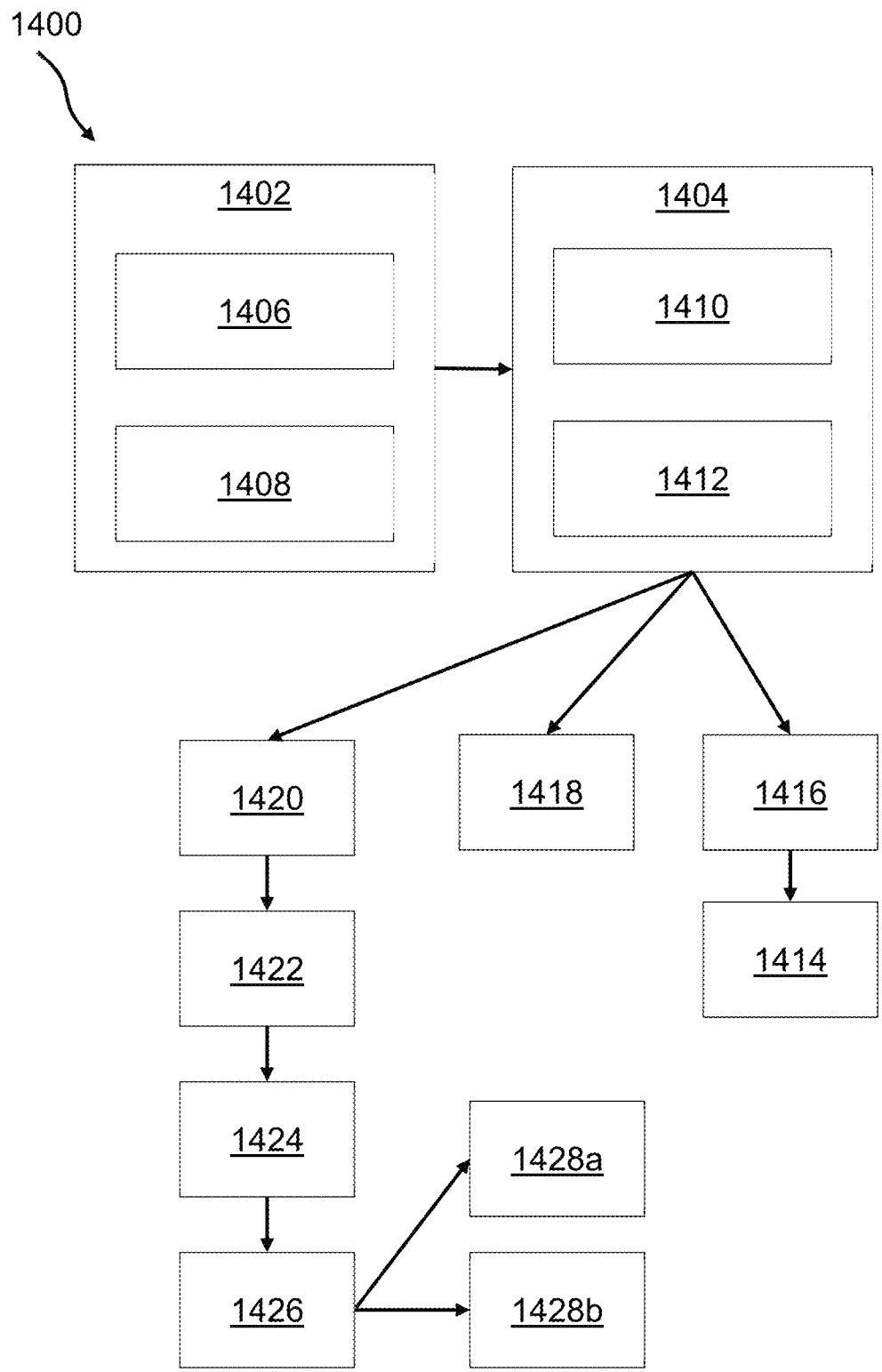
FIG. 14 is a flowchart of an exemplary method

FIG. 14 is a flowchart of an exemplary method 1400 for operating a monitor device, such as a monitor device 6 as described in relation to the previous figures, such as a monitor device configured to be connected to a base plate and/or a sensor assembly part of an ostomy appliance. The base plate and/or the sensor assembly part, has an electrode assembly comprising a plurality of electrodes including a first electrode pair. The monitor device comprises a processor, a memory and a first interface configured for coupling to the electrode assembly of the base plate and/or sensor assembly part. The first interface comprises a plurality of terminals including a first terminal pair configured for forming electrical connections with the first electrode pair of the electrode assembly The method 1400 comprises obtaining 1402 one or more parameters, e.g. from the base plate and/or sensor assembly device, and determining 1404 if one or more operability criteria are satisfied based on the one or more parameters.

For example, the one or more parameters may be indicative of an operating state of the base plate and/or sensor assembly part. For example, the one or more parameters may be indicative of one or more of the electrodes being inoperable or of the monitor device not being fully connected, the battery capacity being low, etc. Thus, the monitor device may be provided with certain minimum requirements for operating, and determining 1404 if one or more operability criteria are satisfied may comprise determining whether such requirements are met.

Obtaining 1402 the one or more parameters includes obtaining 1406 a first parameter of the first terminal pair connected to the first electrode pair of the electrode assembly. For example, obtaining 1406 the first parameter may comprise measuring capacitance and/or resonance frequency of the first electrode pair, such as between the electrodes of the first electrode pair.

Obtaining 1402 the one or more parameters may include obtaining 1408 a second parameter of a second terminal pair connected to a second electrode pair of the electrode assembly. For example, obtaining 1408 the second parameter may comprise measuring capacitance and/or resonance frequency of the second electrode pair, such as between the electrodes of the second electrode pair.

Determining 1404 if the one or more operability criteria are satisfied includes determining 1410 if the first parameter satisfies first operability criteria indicative of operability of the first electrode pair of the electrode assembly. Determining 1404 if the one or more operability criteria are satisfied may further include determining 1412 if the second parameter satisfies second operability criteria indicative of operability of the second electrode pair of the electrode assembly.

The method 1400 further comprises providing 1414 a first monitor device signal indicative of operating failure of the base plate and/or sensor assembly part if the one or more operability criteria are not being satisfied. The provided 1414 first monitor device signal may comprise an audible signal, a tactile signal, and/or a wireless signal to a remote device, such as an accessory device or a remote server.

The method 1400 may further comprise determining 1416 an operating failure type from a set of operating failure types. Thus, in providing 1414 the first monitor device signal, the first monitor device signal may be indicative of the operating failure type, i.e. the system and/or the user may be made aware of a likely cause of the operating failure. For example, the provided 1414 first monitor device signal may be indicative of a component of the ostomy appliance that is one or more of inoperative, damaged, defective, improperly connected, or improperly attached.

The method 1400 may further comprise providing 1418 a second monitor device signal indicative of correct operation of the base plate and/or the sensor assembly part. The second monitor device signal may be provided 1418 in accordance with the operability criteria being satisfied, such as based on that the determination 1404 of if the one or more operability criteria are satisfied has revealed that the operability criteria are satisfied. For example, the user may be provided with notification that the monitor device and/or base plate and/or sensor assembly part are functioning correctly and optionally guidance of intended use of the device(s).

The monitor device may alternatively or additionally be configured in accordance with the obtained 1402 one or more parameters. For example, the obtained 1402 one or more parameters may be indicative of how data should be collected from the base plate and/or sensor assembly part. For example, the one or more parameters may be indicative of one or more of the electrodes being inoperable. Thus, the method 1400 may comprise selecting 1420 a data collection scheme based on the one or more parameters obtained 1402. For example, a first data collection scheme may be selected 1420 if the first operability criteria are not being satisfied and a second data collection scheme may be selected 1420 if the first operability criteria are being satisfied. Furthermore, the method 1400 may comprise selecting 1422 a processing scheme based on the one or more parameters obtained 1402. For example, a first processing scheme may be selected 1422 if the first operability criteria are not being satisfied and a second processing scheme may be selected 1422 if the first operability criteria are being satisfied.

Ostomy data representative of a condition of the base plate and/or sensor assembly part may be collected 1424, and the collecting 1424 of ostomy data may be in accordance with the selected 1420 data collection scheme. The collected 1424 ostomy data is processed 1426 in accordance with the selected 1422 processing scheme.

The processed 1426 ostomy data may be stored 1428*a*, e.g. in memory of the monitor device. The obtained 1402 one or more parameters and/or the collected 1424 ostomy data may also be stored 1428*a*. Alternatively or additionally, the processed 1426 ostomy data may be transmitted 1428*b*, e.g. to a remote device, such as an accessory device and/or a remote server. The obtained 1402 one or more parameters and/or the collected 1424 ostomy data may also be transmitted 1428*b*.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

Exemplary embodiments are set out in the following items:

1. A monitor device of an ostomy system including an ostomy appliance, comprising:
   a processor;
   a memory; and
   a first interface configured for structural coupling to a base plate of the ostomy appliance; and
   wherein the processor is configured to:
      obtain one or more parameters indicative of an operating state of the monitor device and/or the base plate;
      determine if one or more operability criteria are satisfied based on the one or more parameters; and
      provide a first monitor device signal indicative of operating failure of the monitor device and/or the base plate if the one or more operability criteria are not being satisfied.

2. The monitor device according to item 1, wherein the processor is configured to:
   obtain the one or more parameters indicative of an operating state of the monitor device and/or the base plate including by obtaining a first resistor value indicative of a resistance between a first terminal pair of the first interface connected to a respective first terminal pair of the base plate; and
   determine if the one or more operability criteria are satisfied based on the first resistor value.

3. The monitor device according to any of items 1-2, wherein the processor is configured to:
   obtain the one or more parameters indicative of an operating state of the monitor device and/or the base plate including by obtaining a first capacitor value indicative of a capacitance between a first terminal pair of the first interface connected to a respective first terminal pair of the base plate; and
   determine if the one or more operability criteria are satisfied based on the first capacitor value.

4. The monitor device according to any of items 1-3, wherein the processor is configured to:
   obtain the one or more parameters indicative of an operating state of the monitor device and/or the base plate including by obtaining a second resistor value indicative of a resistance between a second terminal pair of the first interface connected to a respective second terminal pair of the base plate; and
   determine if the one or more operability criteria are satisfied based on the second resistor value.

5. The monitor device according to any of items 1-4, wherein the processor is configured to:
   obtain the one or more parameters indicative of an operating state of the monitor device and/or the base plate including by obtaining a first resonance frequency value indicative of a resonance frequency between a terminal pair of the first interface connected to a respective terminal pair of the base plate; and
   determine if the one or more operability criteria are satisfied based on the first resonance frequency value.

6. The monitor device according to any of items 1-5, wherein the processor is configured to:
   obtain the one or more parameters indicative of an operating state of the monitor device and/or the base plate including by obtaining a power parameter value indicative of a power capacity of a power unit of the monitor device; and
   determine if the one or more operability criteria are satisfied based on the power parameter value.

7. The monitor device according to any of items 1-6, wherein the processor is configured to:
   obtain the one or more parameters indicative of an operating state of the monitor device and/or the base plate including by obtaining ostomy data from the base plate via the first interface during a time period that the base plate is applied to a skin surface of the user;
   determine a base plate application parameter indicative of application quality based on the ostomy data; and
   determine if the one or more operability criteria are satisfied based on the base plate application parameter.

8. The monitor device according to any of items 1-7, wherein the processor is configured to:
   obtain the one or more parameters indicative of an operating state of the monitor device and/or the base plate including by obtaining a connection parameter indicative of mechanical connection quality between the monitor device and the base plate; and
   determine if the one or more operability criteria are satisfied based on the connection parameter.

9. The monitor device according to any of items 1-8, wherein the processor is configured to determine an operating failure type from a set of operating failure types, and wherein the first monitor device signal is indicative of the operating failure type.

10. The monitor device according to any of items 1-9, wherein the first monitor device signal indicates that a component of the ostomy appliance is one or more of inoperative, damaged, defective, improperly connected and/or improperly attached.

11. The monitor device according to any of items 1-10, wherein the first monitor device signal is one or more of an audible signal, a tactile signal, or a wireless signal to an accessory device.

12. The monitor device according to any of items 1-11, wherein the processor is configured to, in accordance with the operability criteria being satisfied, provide a second monitor device signal indicative of correct operation of the monitor device and/or the base plate.

13. The monitor device of item 12, wherein the second monitor device signal is one or more of an audible signal, a tactile signal, or a wireless signal to an accessory device.

14. A method of operating a monitor device of an ostomy system to assess the operability of the monitor device and/or a base plate, comprising:
obtaining one or more parameters indicative of an operating state of the monitor device and/or the base plate;
determining if one or more operability criteria are satisfied based on the one or more parameters; and
providing a first monitor device signal indicative of operating failure of the monitor device and/or the base plate if the one or more operability criteria are not being satisfied.

15. The method of item 14, wherein:
obtaining the one or more parameters indicative of an operating state of the monitor device and/or the base plate comprises obtaining a first resistor value indicative of a resistance between a first terminal pair of a first interface connected to a respective first terminal pair of the base plate; and
determining if the one or more operability criteria are satisfied includes determining an operability criterion based on the first resistor value.

16. The method of any of items 14-15, wherein:
obtaining the one or more parameters indicative of an operating state of the monitor device and/or the base plate comprises obtaining a first capacitor value indicative of a capacitance between a first terminal pair of a first interface connected to a respective first terminal pair of the base plate; and
determining if the one or more operability criteria are satisfied includes determining an operability criterion based on the first capacitor value.

17. The method of any of items 14-16, wherein:
obtaining the one or more parameters indicative of an operating state of the monitor device and/or the base plate comprises obtaining a second resistor value indicative of a resistance between a second terminal pair of the first interface connected to a respective second terminal pair of the base plate; and
determining if the one or more operability criteria are satisfied includes determining an operability criterion based on the second resistor value.

18. The method of any of items 14-17, wherein:
obtaining the one or more parameters indicative of an operating state of the monitor device and/or the base plate comprises obtaining a first resonance frequency value indicative of a resonance frequency between a terminal pair of the first interface connected to a respective terminal pair of the base plate; and
determining if the one or more operability criteria are satisfied includes determining an operability criterion based on the first resonance frequency value.

19. The method of any of items 14-18, wherein:
obtaining the one or more parameters indicative of an operating state of the monitor device and/or the base plate comprises obtaining a power parameter value indicative of a power capacity of a power unit of the monitor device; and
determining if the one or more operability criteria are satisfied includes determining an operability criterion based on the power parameter value.

20. The method of any of items 14-19, wherein:
obtaining one or more parameters indicative of an operating state of the monitor device and/or the base plate comprises obtaining ostomy data from the base plate via the first interface during a time period that the base plate is applied to a skin surface of the user; and
the method further includes determining a base plate application parameter indicative of application quality based on the ostomy data; and
determining if the one or more operability criteria are satisfied includes determining an operability criterion based on the base plate application parameter.

21. The method of any of items 14-20, wherein:
obtaining the one or more parameters indicative of an operating state of the monitor device and/or the base plate comprises obtaining a connection parameter indicative of mechanical connection quality between the monitor device and the base plate; and
determining if the one or more operability criteria are satisfied includes determining an operability criterion based on the connection parameter.

22. The method of any of items 14-21, wherein:
the method further includes determining an operating failure type from a set of operating failure types; and
providing the first monitor device signal includes providing the first monitor device signal indicative of the operating failure type.

23. The method of any of items 14-22, wherein the first monitor device signal is indicative of a component of the ostomy appliance that is one or more of inoperative, damaged, defective, improperly connected, or improperly attached.

24. The method of any of items 14-23, wherein providing the first monitor device signal includes providing one or more of an audible signal, a tactile signal, or a wireless signal to an accessory device.

25. The method of any of items 14-24 and further including, in accordance with the operability criteria being satisfied, providing a second monitor device signal indicative of correct operation of the monitor device and/or the base plate.

26. A method of operating a monitor device of an ostomy system including a base plate having a first adhesive layer comprising one or more water soluble or water swellable hydrocolloids for attachment of the base plate to the skin surface of a user and an electrode assembly comprising a plurality of electrodes including a first electrode pair, and wherein the monitor device comprises a processor, a memory and a first interface configured for coupling to the electrode assembly of the base plate, the first interface comprising a plurality of terminals including a first terminal pair configured for forming electrical connections with the first electrode pair of the electrode assembly, the method comprising:
obtaining one or more parameters including obtaining a first parameter of the first terminal pair connected to the first electrode pair of the electrode assembly;
determining if one or more operability criteria are satisfied based on the one or more parameters including determining if the first parameter satisfies first operability criteria indicative of operability of the first electrode pair of the electrode assembly.

27. Method according to item 26 comprising providing a first monitor device signal indicative of a first operating failure state of the electrode assembly if the one or more operability criteria are not being satisfied.

28. Method according to any of items 26-27 comprising selecting a data collection scheme including selecting a first data collection scheme if the first operability criteria are not being satisfied and selecting a second data collection scheme if the first operability criteria are being satisfied.

29. Method according to claim 28, wherein the first data collection scheme is indicative of collection of ostomy data from the plurality of terminals excluding collection of ostomy data from the first terminal pair, and wherein the second data collection scheme is indicative of collection of ostomy data from the plurality of terminals including collection of ostomy data from the first terminal pair.

30. Method according to any of items 26-29 comprising selecting a processing scheme including selecting a first processing scheme if the first operability criteria are not being satisfied and selecting a second processing scheme if the first operability criteria are being satisfied.

31. Method according to any of items 26-30, wherein the first parameter of the first terminal pair is a first capacitor value, indicative of a capacitance between the first terminal pair of the first interface.

32. Method according to any of items 26-31, wherein the first parameter of the first terminal pair is a first resonance frequency value, indicative of a resonance frequency between the first terminal pair of the first interface.

33. Method according to any of items 26-32, wherein the plurality of terminals of the first interface includes a second terminal pair configured for forming electrical connections with a second electrode pair of the electrode assembly, and wherein obtaining the one or more parameters includes obtaining a second parameter of the second terminal pair connected to the second electrode pair of the electrode assembly, and determining if the one or more operability criteria are satisfied includes determining if the second parameter satisfies second operability criteria indicative of operability of the second electrode pair of the electrode assembly.

34. A monitor device of an ostomy system including a base plate having a first adhesive layer comprising one or more water soluble or water swellable hydrocolloids for attachment of the base plate to the skin surface of a user and an electrode assembly comprising a plurality of electrodes including a first electrode pair, the monitor device comprising:
    a processor;
    a memory; and
    a first interface configured for coupling to the electrode assembly of the base plate, the first interface comprising a plurality of terminals including a first terminal pair configured for forming electrical connections with the first electrode pair of the electrode assembly;
    wherein the processor is configured to:
        obtain one or more parameters including obtaining a first parameter of the first terminal pair connected to the first electrode pair of the electrode assembly;
        determine if one or more operability criteria are satisfied based on the one or more parameters including determining if the first parameter satisfies first operability criteria indicative of operability of the first electrode pair of the electrode assembly.

35. Monitor device according to item 34, wherein the processor is further configured to provide a first monitor device signal indicative of a first operating failure state of the electrode assembly if the one or more operability criteria are not being satisfied.

36. Monitor device according to item 35, wherein the first monitor device signal is one or more of an audible signal, a tactile signal, or a wireless signal to an accessory device.

37. Monitor device according to any of items 34-36, wherein the processor is further configured to select a data collection scheme including selecting a first data collection scheme if the first operability criteria are not being satisfied and selecting a second data collection scheme if the first operability criteria are being satisfied.

38. Monitor device according to item 37, wherein the first data collection scheme is indicative of collection of ostomy data from the plurality of terminals excluding collection of ostomy data from the first terminal pair, and wherein the second data collection scheme is indicative of collection of ostomy data from the plurality of terminals including collection of ostomy data from the first terminal pair.

39. Monitor device according to any of items 34-38, wherein the processor is further configured to select a processing scheme including selecting a first processing scheme if the first operability criteria are not being satisfied and selecting a second processing scheme if the first operability criteria are being satisfied.

40. Monitor device according to any of items 34-39, wherein the first parameter of the first terminal pair is a first capacitor value, indicative of a capacitance between the first terminal pair of the first interface.

41. Monitor device according to any of items 34-40, wherein the first parameter of the first terminal pair is a first resonance frequency value, indicative of a resonance frequency between the first terminal pair of the first interface.

42. Monitor device according to any of items 34-41, wherein the first terminal pair comprises a ground terminal and a first terminal, and the ground terminal being configured for forming electrical connections with a ground electrode of the first electrode pair of the electrode assembly, and the first terminal being configured for forming electrical connections with a first electrode of the first electrode pair of the electrode assembly.

43. Monitor device according to any of items 34-42, wherein the plurality of terminals of the first interface includes a second terminal pair configured for forming electrical connections with a second electrode pair of the electrode assembly, and wherein the processor is further configured to:
    obtain the one or more parameters including obtaining a second parameter of the second terminal pair connected to the second electrode pair of the electrode assembly;
    determine if the one or more operability criteria are satisfied based on the one or more parameters including determining if the second parameter satisfies second operability criteria indicative of operability of the second electrode pair of the electrode assembly.

44. Monitor device according to item 43, wherein the second parameter of the second terminal pair is a second capacitor value, indicative of a capacitance between the second terminal pair of the first interface.

45. Monitor device according to any of items 43-44, wherein the second parameter of the second terminal pair is a second resonance frequency value, indicative of a resonance frequency between the second terminal pair of the first interface.

46. Monitor device according to any of items 43-45, wherein the second terminal pair comprises a ground terminal and a second terminal, and the ground terminal being configured for forming electrical connections with a ground electrode of the second electrode pair of the electrode assembly, and the second terminal being configured for forming electrical connections with a second electrode of the second electrode pair of the electrode assembly.

LIST OF REFERENCES 1 ostomy system
2 ostomy appliance 4 base plate
6 monitor device
8 accessory device
10 server device
12 network
14 coupling member
16 coupling ring
18 stoma-receiving opening
20 docking station
22 first connector
24 user interface
50 target device
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver
126 loudspeaker
128 haptic feedback element
140 sensor unit
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
218 masking element
218A distal surface of masking element
218B proximal surface of masking element
220 electrode configuration
222 ground electrode
222A ground connection part
222B ground sensing part
224 first electrode
224A first connection part
224B first sensing part
226 second electrode
226A second connection part
226B second sensing part
228 third electrode
228A third connection part
228B third sensing part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
700 sensor assembly part
800 identifier sensor
816 identifier element

The invention claimed is:

1. A monitor device of an ostomy system, the monitor device comprising:
a processor;
a memory; and
a first interface configured for structural coupling to a base plate of the ostomy system, the first interface coupled to an electrode assembly of the base plate,
wherein the processor is configured to:
obtain one or more parameters indicative of an operating state of at least one selected from the group consisting of the monitor device and the base plate;

determine if one or more operability criteria are satisfied based on the one or more parameters, wherein the one or more operability criteria are associated with operability of an electrode pair of the electrode assembly;

determine an operating failure type of at least one selected from the group consisting of the monitor device and the base plate if the one or more operability criteria are not satisfied, wherein the operating failure type indicates an inability to detect at least one of leakage or adhesive erosion; and provide a first monitor device signal indicative of the operating failure type.

2. The monitor device according to claim 1, further comprising:

a first terminal pair of the first interface connected to a respective first terminal pair of the base plate, wherein the processor is further configured to:

obtain the one or more parameters by obtaining a first resistor value indicative of a resistance between the first terminal pair and the respective first terminal pair; and determine if the one or more operability criteria are satisfied based on the first resistor value.

3. The monitor device according to claim 2, further comprising:

a second terminal pair of the first interface connected to a respective second terminal pair of the base plate, wherein the processor is further configured to:

obtain the one or more parameters by obtaining a second resistor value indicative of a resistance between the second terminal pair and the respective second terminal pair; and determine if the one or more operability criteria are satisfied based on the second resistor value.

4. The monitor device according to claim 1, further comprising:

a first terminal pair of the first interface connected to a respective first terminal pair of the base plate, wherein the processor is further configured to:

obtain the one or more parameters by obtaining a first capacitor value indicative of a capacitance between the first terminal pair and the respective first terminal pair; and determine if the one or more operability criteria are satisfied based on the first capacitor value.

5. The monitor device according to claim 1, further comprising:

a first terminal pair of the first interface connected to a respective first terminal pair of the base plate, wherein the processor is further configured to:

obtain the one or more parameters by obtaining a first resonance frequency value indicative of a resonance frequency between the first terminal pair and the respective first terminal pair; and determine if the one or more operability criteria are satisfied based on the first resonance frequency value.

6. The monitor device according to claim 1, wherein the processor is further configured to:

obtain the one or more parameters by obtaining ostomy data from the base plate via the first interface during a time period that the base plate is applied to a skin surface of a user;

determine, based on the ostomy data, a base plate application parameter indicative of application quality; and determine if the one or more operability criteria are satisfied based on the base plate application parameter.

7. The monitor device according to claim 1, wherein the processor is configured to:

obtain the one or more parameters by obtaining a connection parameter indicative of mechanical connection quality between the monitor device and the base plate; and determine if the one or more operability criteria are satisfied based on the connection parameter.

8. The monitor device according to claim 1, wherein the operating failure type comprises at least one of inoperative, damaged, defective, improperly connected, and improperly attached.

9. The monitor device according to claim 1, wherein:

the first interface comprises a plurality of terminals including a first terminal pair configured for forming electrical connections with a first electrode pair of the electrode assembly;

the base plate comprises a first adhesive layer for attachment of the base plate to a skin surface of a user; and the electrode assembly comprises a plurality of electrodes including the first electrode pair, the plurality of electrodes arranged between the first adhesive layer and a top layer of the base plate.

10. The monitor device according to claim 1, wherein the processor is further configured to:

select a first data collection scheme if the one or more operability criteria are not satisfied, and select a second data collection scheme if the one or more operability criteria are satisfied.

11. A method of operating a monitor device of an ostomy system, the method comprising:

obtaining one or more parameters indicative of an operating state of at least one selected from the group consisting of the monitor device and a base plate of the ostomy system;

determining if one or more operability criteria are satisfied based on the one or more parameters;

determining an operating failure type of at least one selected from the group consisting of the monitor device and the base plate if the one or more operability criteria are not satisfied, wherein the operating failure type indicates an inability to detect at least one of leakage or adhesive erosion; and providing a first monitor device signal indicative of the operating failure type.

12. The method according to claim 11, wherein the monitor device further comprises a first interface having a first terminal pair, the first terminal pair connected to a respective first terminal pair of the base plate, the method further comprising:

obtaining the one or more parameters by obtaining a first resistor value indicative of a resistance between the first terminal pair and the respective first terminal pair; and determining if the one or more operability criteria are satisfied based on the first resistor value.

13. The method according to claim 12, wherein the monitor device further comprises a second terminal pair of the first interface, the second terminal pair connected to a respective second terminal pair of the base plate, the method further comprising:

obtaining the one or more parameters by obtaining a second resistor value indicative of a resistance between the second terminal pair and the respective second terminal pair; and determining if the one or more operability criteria are satisfied based on the second resistor value.

14. The method according to claim 11, wherein the monitor device further comprises a first interface having a first terminal pair, the first terminal pair connected to a respective first terminal pair of the base plate, the method further comprising:
  obtaining the one or more parameters by obtaining a first capacitor value indicative of a capacitance between the first terminal pair and the respective first terminal pair; and
  determining if the one or more operability criteria are satisfied based on the first capacitor value.

15. The method according to claim 11, wherein the monitor device further comprises a first interface having a first terminal pair, the first terminal pair connected to a respective first terminal pair of the base plate, the method further comprising:
  obtaining the one or more parameters by obtaining a first resonance frequency value indicative of a resonance frequency between the first terminal pair and the respective first terminal pair; and
  determining if the one or more operability criteria are satisfied based on the first resonance frequency value.

16. The method according to claim 11, further comprising:
  obtaining the one or more parameters by obtaining a connection parameter indicative of mechanical connection quality between the monitor device and the base plate; and
  determining if the one or more operability criteria are satisfied based on the connection parameter.

17. The method according to claim 11, further comprising:
  selecting a first data collection scheme if the one or more operability criteria are not satisfied, and
  selecting a second data collection scheme if the one or more operability criteria are satisfied.

18. The method according to claim 11, wherein the operating failure type comprises at least one of inoperative, damaged, defective, improperly connected, and improperly attached.

19. The method according to claim 11, further comprising:
  obtaining the one or more parameters by obtaining ostomy data from the base plate via a first interface of the monitor device during a time period that the base plate is applied to a skin surface of a user;
  determining, based on the ostomy data, a base plate application parameter indicative of application quality; and
  determining if the one or more operability criteria are satisfied based on the base plate application parameter.

20. The method according to claim 19, wherein:
  the first interface comprises a plurality of terminals including a first terminal pair configured for forming electrical connections with a first electrode pair of an electrode assembly of the base plate;
  the base plate comprises a first adhesive layer for attachment of the base plate to the skin surface of the user; and
  the electrode assembly comprises a plurality of electrodes including the first electrode pair, the plurality of electrodes arranged between the first adhesive layer and a top layer of the base plate.

* * * * *